US005168045A

United States Patent [19]

Dyer et al.

[11] Patent Number: 5,168,045

[45] Date of Patent: Dec. 1, 1992

[54] DIAGNOSTIC SYSTEMS AND METHODS USING POLYPEPTIDE ANALOGS OF APOLIPOPROTEIN E

[75] Inventors: Cheryl A. Dyer, Poway; Linda K. Curtiss, San Diego; Richard Smith, Del Mar, all of Calif.

[73] Assignee: The Scripps Research Institute, La Jolla, Calif.

[21] Appl. No.: 540,363

[22] Filed: Jun. 18, 1990

Related U.S. Application Data

[63] Continuation-in-part of Ser. No. 485,158, Feb. 26, 1990, which is a continuation-in-part of Ser. No. 395,732, Aug. 18, 1989.

[51] Int. Cl.[5] .......... G01N 33/53

[52] U.S. Cl. .......... 435/7.92; 435/7.93; 435/7.94; 436/518; 530/387.9; 530/391.1; 530/389.3

[58] Field of Search .......... 530/387, 387.9, 389.1, 530/391.1, 389.3; 436/518, 7.92; 435/7.93, 7.94

[56] References Cited

U.S. PATENT DOCUMENTS

| | | | |
|---|---|---|---|
| 4,643,988 | 2/1987 | Segrest et al. | 514/12 |
| 4,677,057 | 6/1987 | Curtiss et al. | 436/518 |
| 4,828,986 | 5/1989 | Smith et al. | 435/7.94 |
| 4,877,746 | 10/1989 | Jansson et al. | 436/518 |
| 4,970,144 | 11/1990 | Fareed et al. | 435/5 |

OTHER PUBLICATIONS

Gesquiere et al., Clin. Chem. 31 (5): 784–785, 1985.
Expand et al., *J. Biol. Chem.*, 262:9389–9396 (1987).
Segrest, FEBS Lett., 38:247–253 (1974).
Mahley, et al., *Biochim. Biophy. Acta.*, 737:197–222 (1983).

*Primary Examiner*—Esther L. Kepplinger
*Assistant Examiner*—Donna Wortman
*Attorney, Agent, or Firm*—Douglas A. Bingham; Thomas Fitting; April C. Logan

[57] ABSTRACT

Apo E polypeptides capable of mimicking apolipoprotein E are described that are useful to prepare diagnostic antibodies, and for use in diagnostic systems and methods for detecting apo E antigens in vascular body fluids.

15 Claims, 3 Drawing Sheets

FIG. 1a
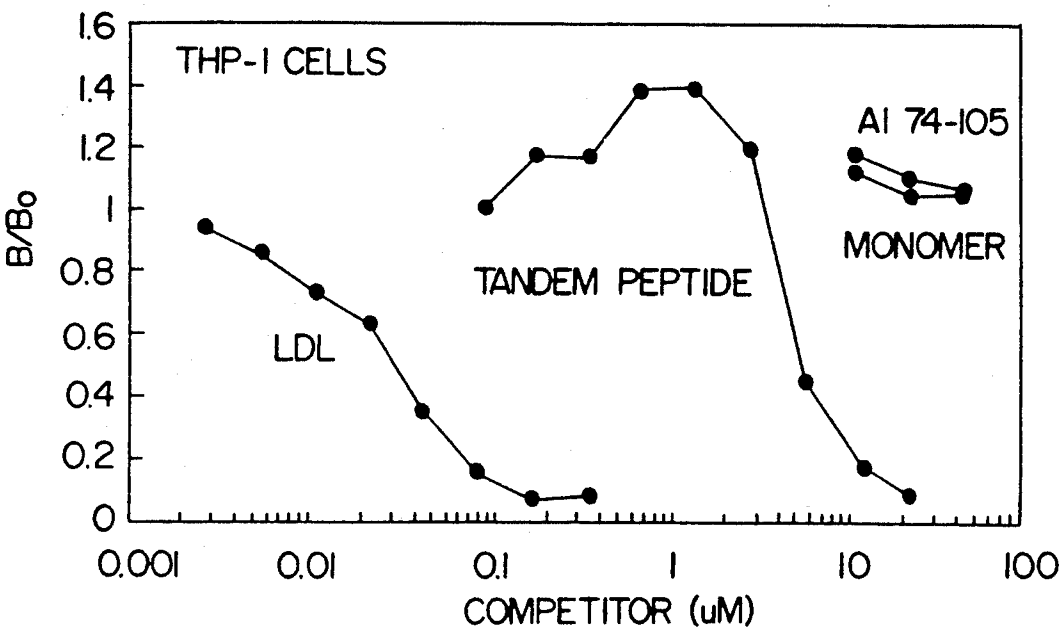
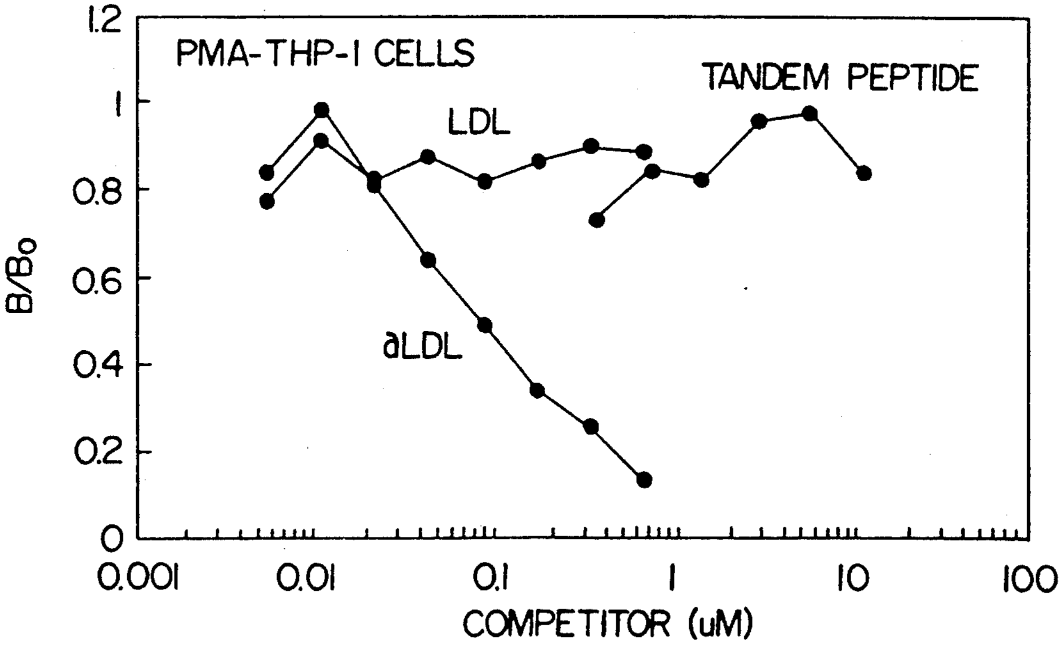
FIG. 1b

DIAGNOSTIC SYSTEMS AND METHODS USING POLYPEPTIDE ANALOGS OF APOLIPOPROTEIN E

This invention was made with government support under National Institutes of Health Contract HL-35297 R01. The government has certain rights in the invention.

CROSS REFERENCE TO RELATED APPLICATIONS

This is a continuation-in-part of U.S. patent application Ser. No. 07/485,158, filed Feb. 26, 1990, which is a continuation-in-part of U.S. patent application Ser. No. 07/395,732, filed Aug. 18, 1989, the disclosures of which are hereby incorporated by reference.

DESCRIPTION

1. Technical Field

The present invention relates to enhancement of cholesterol clearance mediated by receptor-binding (receptor-competent) polypeptides capable of mimicking apolipoprotein (apo) E. More particularly, the present invention relates to the use of synthetic tandem peptides to modulate hepatic (and other cell) uptake of cholesterol-containing proteins and to diagnostic methods using these peptides and their antibodies to evaluate efficacy of these therapeutic measures.

2. Background

Lipoproteins are the primary carriers of plasma cholesterol. They are micellar lipid-protein complexes (particles), having a surface film comprised of one or more proteins associated with polar lipids, that surrounds a cholesterol-containing core. Original classification of lipoproteins was based on their buoyant densities as measured by ultracentrifugation. Accordingly, four major density classes have been recognized, and subclasses within these exist.

The first class comprises the chylomicrons. They are the largest of the lipoproteins and are rich in triglycerides. The site of origin of the chylomicrons is the intestine. When chylomicrons are exposed to plasma or high density lipoprotein (HDL) in vitro, much of their complement of A apolipoproteins is lost, and C and E apolipoproteins are acquired. Chylomicrons also contain apolipoprotein B-48.

The next class of lipoproteins, the very low density lipoproteins (VLDL), is comprised of particles made in the liver and involved in triglyceride metabolism and transport from the liver. The apolipoproteins, apo B-100 and apo E, are the major constituents of the VLDL particle.

The third lipoprotein class, comprising low density lipoproteins (LDL), is a specific product of the catabolism of VLDL. The predominant apolipoprotein in LDL particles is apolipoprotein B-100, or apo B-100.

The fourth class, high density lipoprotein (HDL) contains two major apolipoproteins, apo A-I and apo A-II. One function of apo A-I is the activation of the plasma enzyme, lecithin-cholesterol acyltransferase, which is required for the esterification of free cholesterol on HDL for transport to the liver.

Plasma cholesterol is regulated in part by the LDL receptor and in part on the ability of the lipoprotein to carry cholesterol and bind the LDL receptor. Hofmann, et al., *Science,* 239:1277 (1988). This receptor is found on the surface of all cells where it mediates binding and internalization of the cholesterol-rich lipoproteins that provide membrane cholesterol; Brown, et al., *J. Clin. Invest.,* 55:783 (1975); Goldstein, et al., *Methods Enzymol.,* 98:241 (1983); and in some specialized cells substrate cholesterol for the production of bile acids or steroid hormones; Gwynne, et al., *Endocr. Rev.,* 3:299 (1982). LDL receptor expression on cells is inversely regulated by the circulating concentration of LDL, i.e., the higher the circulating LDL the fewer LDL receptors on the cell surface Hofmann, et al., *Science,* 239:1277 (1988). LDL binding to the LDL receptor has been the focus of much research because of its importance in regulating the level of plasma cholesterol, which is considered a major risk factor for the development of coronary artery disease; Brown, et al., *Scient. Amer.,* 251:58 (1984).

LDL binding to the LDL receptor is believed to be dependent upon the species of apolipoprotein present in the lipoprotein particle.

Apolipoproteins are lipid-free protein components of plasma or serum lipoproteins obtained by treating intact lipoproteins with organic solvents, detergents, or chaotropic agents. Not all proteins captured with lipoproteins necessarily have a role in lipid transport. A pertinent example is the recent recognition that serum amyloid A proteins, acute phase reactants, are transported in plasma bound to HDL. These low molecular weight proteins may comprise up to 30 percent of apo-HDL in inflammatory states, but it is doubtful that they have specific lipid transport roles.

Apo B-100 is recognized and bound by cell LDL receptors. By binding to apo B-100, these receptors extract LDL particles from plasma. The LDL is thereby taken into a cell and broken down, yielding its cholesterol to serve the cell's needs. The interaction between apo B-100 and the LDL receptor thus plays a major role in removal of LDL cholesterol from the bloodstream. All LDL particles contain apo B-100.

When compared to apolipoproteins A-1 or B, the relative concentration of apo E in plasma is low. However, apo E is instrumental in lipoprotein metabolism in several ways. Mahley, et al., *J. Lipid Res.,* 25:1277–1294 (1984). It is a recognition site for several cellular lipoprotein receptors, including hepatocyte receptors for chylomicron and VLDL remnants [Hui, et al., *J. Biol. Chem.,* 259:860–869 (1984); Shelburne, et al., *J. Clin. Invest.,* 65:652–658 (1980)], receptors for LDL on hepatic and extrahepatic cells [Hui, et al., *J. Biol. Chem.,* 256:5646–5655 (1981)] and receptors for VLDL on macrophages [Wang-Iverson et al., *Biochem. Biophys. Res. Commun.,* 126:578–586 (1985)].

Apo E may also play a role in lipoprotein lipase-mediated lipolysis of lipoproteins [Yamada, et al., *Biochem. Biophys. Res. Commun.,* 94:710–715 (1980); Ehnholm, et al., *Proc. Natl. Acad. Sci. USA,* 81:5566–5570 (1984)] and facilitate transport of sterols under certain conditions [Fielding et al., *Metabolism,* 31:1023–1028 (1982)].

About half of apo E is associated with VLDL and the other half with HDL-sized particles. Gibson, et al., *Biochem. Biophys. Acta.,* 835:113–123 (1985). There is virtually no apo E in plasma which is not associated with lipoproteins.

There are significant differences in the disposition of certain apo E epitopes on various lipoproteins, affecting their physiological functions. The immunochemical data are in accord with observations that lipoprotein lipids do modulate the conformation of apo E, as detected by circular dichroism [Chen, et al., *Biochemistry*, 23:6530-6538 (1984)] and optical rotary dispersion [Klimov, et al., *Mol. Biol.*, 18:404-409 (1984)]. The heterogeneity of apo E conformation or disposition on the surfaces of lipoproteins is also confirmed by the varying accessibility to thrombin cleavage of apo E on differently sized VLDL particles. Bradley, et al., *J. Biol. Chem.*, 259:14728-14735 (1984)., Lipoproteins are cleared from the plasma by binding to high-affinity receptors on liver cells and extrahepatic tissues such as the adrenal glands and ovaries. Kowal, R. C. et al., *Proc. Natl. Acad. Sci. USA*, 86:5810-5814, (1989). The LDL receptor specifically binds apo B and apo E-bearing lipoproteins. R. W. Mahley, *Science*, 240:622 (1988). Thus, apo E is of clinical importance for its role in binding LDL receptor and facilitating cholesterol clearance.

The LDL receptor-binding region of apo E has been mapped to an internal sequence including amino acid residues 140 to 160. Weisgraber, et al., *J. Biol. Chem.* 258:12348 (1983). Additionally, apo E binds the LDL receptor only when it is associated with a lipoprotein or phospholipid [Innerarity, et al., *J. Biol. Chem.*, 254:4186 (1979)] and 4 apo E molecules bind the LDL receptor with an affinity that is 10 to 25-fold greater than the binding of a single molecule of apo B. R. W. Mahley, *Science*, 240:622 (1988).

Two distinct sets of receptors bind apo E-containing lipoproteins. The LDL receptor [Yamamoto et al., *Cell*, 39:27-38 (1984)], 70% of which is thought to be located on hepatic cells, binds VLDL and apo E-containing remnants of chylomicrons. The existence of a second set of LDL receptors, termed "remnant receptors", is inferred from studies showing that the plasma clearance of apo E-containing chylomicron remnants occurs at normal rates in animals with genetically defective LDL receptors.

Recently, an LDL receptor-related protein (LRP) has been found on the surface of hepatic cells. Herz et al., *EMBO*, 7:4119-4127 (1988). LRP shares cysteine-repeat sequences with LDL and has been shown to bind and mediate the extracellular clearance of apo E-containing lipoproteins. Kowal, R. C. et al. *Proc. Natl. Acad. Sci. USA*. 86:5810-5814, (1989).

Apo E-enriched lipoproteins have also been described to have a function in the immune system by inhibiting mitogen-or antigen-stimulated lymphocyte proliferation in vitro and in vivo. In vitro this activity is observed at concentrations of 10 ug/ml. A lipid-free thrombin fragment of apo E that contains amino acids 1-219 is active in modulating lymphocyte proliferation. Pepe, et al., *J. Immunol.*, 136:3716 (1986). In the ovary, apo E inhibits androgen production by LH-stimulated cultured theca and interstitial cells; Dyer, et al., *J. Biol. Chem.*, 263:10965 (1988). Until recently the domain of apo E responsible for the inhibition of steroidogenesis has not been investigated. However, lipid-free apo E is active.

Plasma lipoproteins differ from most humoral immunoregulatory molecules in that they are large heterogenous non-covalent complexes of lipid and protein. An important step to understanding the mechanism of lipoprotein regulation of cell function is an identification of the constituent(s) of the lipoprotein particle that mediate the observed biologic effects. Plasma lipoproteins contain various amounts of apoproteins, glyceride, free and esterified cholesterol, phospholipid, glycolipid and free fatty acid. Many of these constituents of lipoproteins can by themselves influence cell function.

Cardin et al., *Biochem. Biophys. Res. Comm.*, 154:741-745 (1988) reported that a polypeptide portion of apo E having an amino acid residue sequence identical to that of apo E residues 141-155 inhibits lymphocyte proliferation when coupled to bovine serum albumin (BSA). However, conspicuously absent from the study of Cardin et al. was any control for cell viability allowing for a determination of whether or not the inhibition observed was due to cytotoxicity of the peptide-BSA conjugate.

Several immunoassays developed for detecting apo E have been described in recent publications. Widely differing concentrations of human apo E in plasma have been reported by researchers using polyclonal antisera in quantitative immunoassays, probably because different standards and antisera have been used. Greg et al., *NIH Publication*, 83-1266 (1983). Most assays require the use of denaturants or detergents to "expose" all apo E epitopes in human plasma and in isolated lipoproteins. This may be because most of the antisera are produced by immunization with isolated apo E, which tends to self-aggregate [Greg et al., *NIH Publication*, 83-1266 (1983),; Havel, et al., *J. Clin. Invest.*, 66:1351-1362 (1980)] and to form hetero- and homodimers via disulfide bridges. Tada, et al., *Biochem. Biophys. Res. Comm.*, 90:297-304 (1979).

Because it is highly likely that these antisera contain antibody populations directed against apo E epitopes that are non-existent or "masked" in lipid-rich lipoproteins, the use of detergents or denaturants in plasma or intact lipoprotein samples is necessary, further compounding the problem.

BRIEF SUMMARY OF THE INVENTION

It has now been discovered that the amino acid residue sequence corresponding to residues 141-155 of mature apo E can mimic the biological activity of apo E only when present as a multimeric peptide or a self-conjugate. A multimeric apo E polypeptide is useful for preparing antibodies, and in diagnostic methods to monitor the amounts of apo E antigens in a vascular body fluid.

This one aspect contemplated by this invention is a composition comprising antibody molecules that immunoreact with a polypeptide containing a plurality of segments each having an amino acid residue sequence corresponding to the formula LRKLRKRLLRDADDL (p141-155) and apo E/VLDL, but do not immunoreact with the polypeptide p93-112 or p172-182 and preferably do not immunoreact with a polypeptide containing only a monomer of p141-155.

Further contemplated is a method for detecting apo E antigens in a vascular fluid sample by admixing the sample with an anti-apo E antibody to form an immunoreaction admixture, the antibody preferably being operatively linked to a solid support such that the immunoreaction admixture has both a liquid phase and a solid phase, and said antibody containing antibody molecules that immunoreact with a polypeptide containing a plurality of segments each having an amino acid residue sequence corresponding to the formula LRKLRKRLLRDADDL and with apo E/VLDL but do not immunoreact with the polypeptide p93-112 or p172-182, and preferably does not immunoreact with a polypeptide containing only a monomer of p141-155.

This immunoreaction admixture is maintained under biological assay conditions for a time period sufficient to form an apo E immunoreaction product. Thereafter the amount of immunoreaction product thus formed is detected, and thereby the amount of apo E antigen present in the vascular fluid sample, is determined.

In a more preferred embodiment, the detecting step is accomplished by admixing a labeled specific binding agent capable of binding an apo E-containing lipoprotein particle with the apo E-containing immunoreaction product to form a labeling reaction admixture, and maintaining this admixture under biological assay conditions for a time period sufficient for the labeled specific binding agent to bind the apo E-containing immunoreaction product to form a labeled complex which can be detected.

In a most preferred embodiment, the labeled specific binding agent is a monoclonal anti-B-100 antibody produced by the hybridoma having ATCC designation HB 8746.

A method for detecting an apo E antigen in a vascular fluid sample is also contemplated, comprising the steps of (i) admixing a vascular fluid sample with a solid phase-bound apo E peptide analog containing a plurality of segments each having an amino acid residue sequence corresponding to the formula LRKLRKRLLRDADDL to form a first solid-liquid phase admixture; (ii) admixing an antibody composition, containing a limiting amount of anti-apo E peptide antibody molecules of this invention that immunoreact with the apo E antigen, with the first admixture to form a second admixture; (iii) maintaining the second admixture under biological assay conditions for a period of time sufficient to form an apo E peptide antigen-containing immunoreaction product in the solid phase; and (iv) determining the amount of immunoreaction product present in the solid phase formed and, thereby, the amount of the apo E antigen in the fluid.

In a preferred embodiment, the reveal anti-apo E antibody is operatively linked to an enzyme indicating means, and the product formed is a labeled immunoreaction product.

Still further contemplated is a diagnostic system, in kit form, comprising, in an amount sufficient to perform at least one assay, an antibody composition containing anti-apo E antibody molecules that immunoreact with a polypeptide containing a plurality of segments each having an amino acid residue sequence corresponding to the formula LRKLRKRLLRDADDL, and with apo E/VLDL, but do not immunoreact with the polypeptides p73-112 or p172-182, and preferably do not immunoreact with a polypeptide containing only a monomer of p141-155.

In the case where apo B-100 is to be used as a marker for detection, a reveal antibody composition containing anti-apo B-100 antibody molecules is included.

In a preferred embodiment, the capture antibody molecules are operatively linked to a solid matrix, and the reveal antibody molecules are operatively linked to an enzyme indicating means.

Still further contemplated is a method for monitoring the efficacy of a therapeutic regimen for facilitating cholesterol clearance. This method comprises (i) determining the total amount of apo E components in vascular fluid, and (ii) determining the amount of effective apo E associated with cholesterol-containing lipoprotein particles in vascular fluid. Thus, the total apo E receptor-competent apo E ratio is determined, and the resultant ratio is related to predetermined concentration levels that have previously been correlated to degree of cholesterol clearance efficiency.

BRIEF DESCRIPTION OF THE DRAWINGS

FIG. 1 illustrates that tandem apo E peptide $p(141-155)_2$ affects LDL binding and degradation in a dose dependent, biphasic manner as determined in Example 3. In FIG. 1A, increasing concentrations of competitor comprising tandem apo E peptide $p(141-155)_2$, LDL, control monomer p141-155 or control p74-105 were added to cultures of THP-1 cells simultaneously with the addition of $^{125}$I-LDL. The disappearance of acid soluble $^{125}$I-LDL was followed over a five-hour incubation at 37° C. Each point represents the average radioactivity from 4 wells per treatment. Standard deviation was less than 10% for all means.

FIG. 1B shows the specificity of tandem peptide binding to LDL receptors. THP-1 cells were stimulated with PMA for 4 days. LDL was acetylated, radiolabeled, and TCA precipitable. After 5 hours at 37° C., the $B/B_o$ ratios were analyzed. Neither LDL or tandem peptide inhibited degradation of $^{125}$I-aLDL, but the tandem peptide caused an 80% inhibition of $^{125}$I-LDL degradation.

DETAILED DESCRIPTION OF THE INVENTION

A. Definitions

Figure 2:
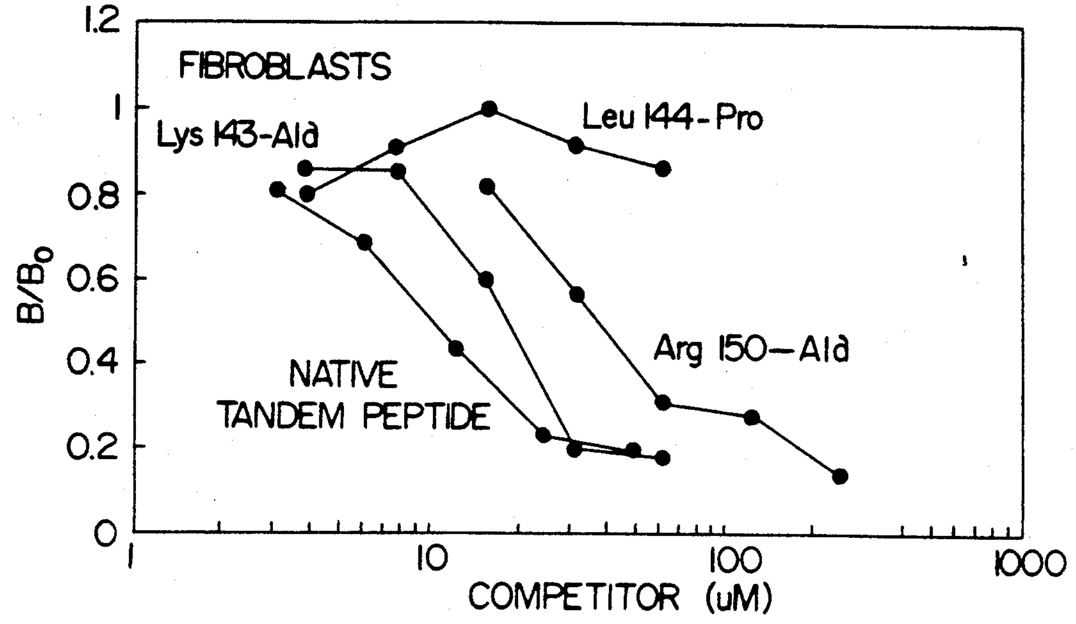
FIG. 2 illustrates that specific amino acid substitutions in the tandem peptide alter its ability to inhibit $^{125}$I-LDL binding to fibroblasts when measured as described in Example 4. Each point is the average of 3 replicates per treatment with the SEM$<$10%.

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE SYMBOL 1-Letter | 3-Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Protein: refers to a linear series of greater than 50 amino acid residues connected one to the other as in a polypeptide.

Synthetic peptide: refers to a chemically produced chain of amino acid residues linked together by peptide bonds that is free of naturally occurring proteins and fragments thereof.

B. Apo E Polypeptide

The present invention contemplates a polypeptide capable of substantially mimicking the ability of apo E to induce differentiated cellular function, such as hepatic LDL degradation, lymphocyte proliferation, androgen secretion by ovarian theca and interstitial cells, and the like. That is, a subject polypeptide acts as an analog of apo E at least with regard to the ability of apo E to inhibit lymphocyte proliferation and/or ovarian androgen secretion, and increase the uptake of LDL by hepatocytes.

A subject polypeptide is further characterized by the presence of a plurality of apo E-derived segments (regions) within the polypeptide's primary structure, each of the segments being defined by a sequence of amino acid residues corresponding to the formula:

Leu-Arg-Lys-Leu-Arg-Lys-Arg-Leu-Leu-Arg-Asp-Ala-Asp-Asp-Leu, also referred to as p(141-155) because the amino acid residue sequence corresponds to residues 141 through 155 of the native apo E protein.

The apo E-derived segments are capable of binding to the LDL receptor and/or LDL receptor-related protein [Herz et al., *EMBO Journal,* 7:4119-4129 (1988)] as evidenced by the ability of the binding to be competitively inhibited. The apo E-derived segments can be adjacent and/or contiguous within the polypeptide chain, with adjacent segments being separated in the amino acid residue sequence of the polypeptide by one or more spacing residues. Preferably, the spacing residues make up a spacing segment in the range of about 1 to about 20, preferably about 5 to about 15, and more usually about 10, amino acid residues in length.

In addition, a subject polypeptide can contain a leader segment of 1 conveniently up to about 33, such as about 11, about 18 or about 22, amino acid residues located amino-terminal to the amino-terminal apo E-derived or spacing segment.

In a similar manner, a subject polypeptide need not end with the carboxy-terminal residue of an apo E-derived segment or spacer segment. A carboxy terminal tail segment can be present containing 1 conveniently up to about 33, such about 11, about 18 or about 22, amino acid residues.

Preferred polypeptides of the present invention are therefor defined by formula I:

B—(X$_n$—Leu—Arg—Lys—Leu—Arg—Lys—Arg—Leu—Leu—Arg—Asp—Ala—Asp—Asp—Leu—Z$_m$)$_a$—J.

In the above formula, B is an amino-terminal $NH_2$ group or a previously discussed leader segment; J is a carboxy-terminal COOH group or a previously discussed tail segment; X and Z are first and second, respectively, spacing segments whose amino acid residue sequences can be the same or different; n is either 1 or 0 such that when n is 1, X is present, and when n is 0, X is not present; m is either 1 or 0 such that when m is 1, Z is present, and when m is 0, Z is not present; and a is an integer from 2 to about 10, more preferably 2 to about 5 and usually 2 to 3, indicating the number of times the amino acid residue sequence in parenthesis is present (repeated) in the polypeptide primary structure. Preferably, the sequence in parenthesis corresponds in its entirety, and preferably is identical to, a portion of the amino acid residue sequence of apo E. Preferred polypeptides are those whose formulas are shown in Table 1.

TABLE 1

| Designation Sequences | Amino Acid Residue |
|---|---|
| p(141-155)$_2$ | LRKLRKRLLRDADDLLRKLRKRLLRDADDL |
| p(129-163)$_2$ | STEELRVRLASHLRKLRKRLLRDADDLQKRLAVYQSTEELR-VRLASHLRKLRKRLLRDADDLQKRLAVYQ |

It should be noted that p(129-163)$_2$ contains a 12 residue leader segment STEELRVRLASH (residues 1-12), a 20 residue spacing segment QKRLAVYQSTEELR-VRLASH (residues 28-47) and an 8 residue tail segment QKRLAVYQ (residues 63-70). The designation p(141-155)$_2$ defines a tandem apo E peptide which contains two adjacent sequences of the p141-155 segment. An additional preferred polypeptide is a "trimer" containing three adjacent sequences of the p141-155 segment, designated 141-155)$_3$. Preferred also are self-conjugates of the tandem apo E peptides designated $p(141-155)_2$-$p(141-155)_2$ and trimer apo E peptides designated $p(141-155)_3$-$p(141-155)_3$.

A subject polypeptide typically contains a total of about 30 to about 450 amino acid residues, preferably about 60 to about 120 residues. Typically, a subject polypeptide contains no more than about 100, preferably no more than about 70 and usually no more than about 30 or 40 amino acid residues in its primary sequence.

A subject polypeptide includes any analog, fragment or chemical derivative of a polypeptide whose amino acid residue sequence is shown herein so long as the polypeptide is capable of inducing differentiated cellular function in a manner corresponding to that of apo E. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability to mimic apo E as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

A subject polypeptide can be prepared using recombinant nucleic acid methodologies well known in the art. For instance, DNA sequences useful in producing a subject polypeptide are described in Paik et al., *Proc. Natl. Acad. Sci. USA*, 82:3445-3449, (1985); McLean et al., *J. Biol. Chem.*, 259:6498-6504, (1984); and Rall et al., *J. Biol. Chem.*, 257:4171-4178, (1982). A DNA segment coding for a polypeptide of this invention can be synthesized by chemical techniques, for example the phosphotriester method of Matteucci et al., *J. Am. Chem. Soc.*, 103:3185, (1981). The DNA segment can then be ligated into an expression vector, and a host transformed therewith can be used to produce the polypeptide. See, for example, *Current Protocols In Molecular Biology*, Ausubel et al., eds., John Willey & Sons, New York, N.Y.; U.S. Pat. Nos. 4,237,224 and 4,356,270.

The recombinant expression vectors capable of expressing a subject polypeptide and methods of their use for producing a subject polypeptide are contemplated as part of the present invention.

A subject polypeptide can also be prepared using the solid-phase synthetic technique initially described by Merrifield, in *J. Am. Chem. Soc.*, 85:2149-2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, IL, 3d Ed., Neurath, H. et al., Eds., p. 104-237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

C. Conjugates

The present invention further contemplates an apo E analog in the form of a polypeptide conjugate comprised of a plurality of polypeptides operatively linked, by other than a peptide bond between the alpha-amino group and carboxy group of contiguous amino acid residues, where at least two of the linked polypeptides have an amino acid residue sequence corresponding to that represented by the formula:

B—($X_n$—Leu—Arg—Lys—Leu—Arg—Lys—Arg—Leu—Leu—Arg—Asp—Ala—Asp—Asp—Leu—$Z_m$)$_a$—J.

wherein B, X, Z, J, n, m and a are defined as previously discussed except that a can also be the integer 1.

Preferred self-conjugates are p141-155 linked to p141-p155, designated (p141-155)-(p141-155) and p129-163 linked to p129-163, designated (p129-163)-(p129-163).

In preferred embodiments, a conjugate of this invention has a molecular weight of less than about 40,000 daltons, preferably less than about 20,000 daltons, and more preferably less than about 10,000 daltons. Typically, a subject conjugate has a molecular weight of no more than about 15,000 daltons, preferably no more than about 8,000 daltons, and usually no more than about 4,000 daltons. Preferably, the conjugate is dimeric or trimeric, i.e., consists essentially of two or three polypeptide chains, respectively.

A polypeptide conjugate of this invention is further characterized by its ability to substantially mimic apo E's ability to induce differentiated cellular function, such as lymphocyte proliferation, ovarian androgen secretion, and the like. The subject conjugates are also substantially free of toxicity toward lymphocytes and androgen-producing ovarian (theca/interstitial) cells at concentrations of about 20 micrograms per milliliter (ug/ml).

The techniques of polypeptide conjugation or coupling through activated functional groups presently known in the art are particularly applicable. See, for example, Aurameas, et al., *Scand. J. Immunol.*, Vol. 8, Suppl. 7:7-23 (1978) and U.S. Pat. Nos. 4,493,795, 3,791,932 and 3,839,153. In addition, a site directed coupling reaction can be carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

D. Compositions for Modulating Hepatic LDL Degradation

In view of the ability of the polypeptides and conjugates of the present invention to bind the LDL receptor present on hepatocytes, the present invention contemplates a composition for modulating hepatic uptake of LDL. The composition comprises an LDL receptor-binding moiety operatively linked to an LDL binding moiety. The LDL receptor-binding moiety comprises a polypeptide and/or conjugate of the present invention. A preferred LDL receptor-binding moiety comprises the polypeptide segment designated p(141-155)$_2$ whose amino acid residue sequence is shown in Table 1.

The LDL receptor-binding moiety can be operatively linked to the LDL binding moiety by a peptide bond or through a covalent bond that is not a peptide bond between the alpha-amino group and carboxyl group of continuous amino acid residues.

An LDL binding moiety can be an anti-LDL antibody molecule or immunologically active fragment thereof. Exemplary anti-LDL-antibody molecules are produced by hybridomas HB8746 and HB8742, which have been deposited with the *American Tissue Culture Collection* (ATCC; Rockville, Md.), both of which produce anti-apo B-100 antibody molecules. The LDL receptor-binding polypeptide and/or conjugate of this invention can be chemically coupled as described hereinbefore to the anti-LDL antibody molecule. Alternatively, a polypeptide of this invention can be incorporated into the primary amino acid residue sequence of the antibody molecule by recombinant DNA techniques. Typically, the LDL receptor-binding polypeptide will be incorporated into or substituted for a portion of one of the antibody molecule's constant domains. See U.S. Pat. Nos. 4,816,567, 4,816,397 and 4,647,334.

In preferred embodiments, the LDL binding moiety is a lipophilic (hydrophobic) sequence of amino acid residues. More preferably, the LDL binding moiety is a polypeptide segment having an amino acid residue sequence capable of forming an amphipathic helix.

Of course, when the means for operatively linking the LDL receptor moiety and LDL binding moiety is other than a peptide bond, the linking typically occurs between amino acid residue chains on residues at or near the carboxy-and/or amino-terminus of the respective moieties so as to preserve their activities.

Preferred helical amphipathic polypeptide segments of this invention, whether incorporated into the composition by a peptidic or non-peptidic bond, include those having an amino acid residue sequence corresponding to that of an apolipoprotein, such as apo B-100, apo B-48, apo C-I, apo C-II, apo C-III, apo A-I, apo A-II, apo D, apo E and the like. See, Fitch, *Genetics*, 86:623-644 (1977); Segrest et al., *Biopolymers*, 16:2053-2065 (1977); and Chan, *Klin Wochenscher*, 67:225-237 (1989). By using a helical amphipathic polypeptide segment with amino acid residue sequence derived from apo B-100 or apo B-48, the polypeptide can be preferentially targeted to LDL as opposed to other lipoprotein species.

The amphipathic helix is characterized by a spacial segregation of hydrophobic and hydrophilic amino acid residues on opposite faces of the helix. The clustered nonpolar residues can then intercalate into lipid particles such as LDL. In addition to this hydrophobic interaction, there may also be specific charge interactions between lipid and peptide. For example, it has been demonstrated that an 18-residue peptide can bind to phospholipid if it has positively charged residues at the hydrophobic-hydrophilic interface of an amphipathic helix and negatively charged residues opposite the hydrophobic face of the helix. See Epand et al., *J. Biol. Chem.*, 264:4628-4635 (1989).

A particularly preferred helical amphipathic polypeptide segment useful in binding the apo E-derived polypeptide segment LDL receptor-binding moiety to LDL has an amino acid residue sequence corresponding to the formula:

EWLKAFYEKVLEKLKELF.

In preferred embodiments, the composition is a polypeptide according to formula I wherein B and/or J is a helical amphipathic polypeptide segment as described above. One preferred polypeptide of this type has an amino acid residue sequence corresponding to the formula:

LRKLRKRLLRDADDLLRKLRKRLLRDADDL—
EWLKAFYEKVLEKLKELF.

In preferred embodiments, the subject polypeptide or conjugate is dispersed in a carrier, such as a phospholipid. More preferably, the subject polypeptide or conjugate is removably inserted in a liposome, i.e., it is incorporated (anchored) into the liposome bilayer via the LDL binding moiety. See, for example, Gregoriadis, *Trends in Biotech.*, 3:235-241 (1985) and Eriksson et al., pp 141-156 in *Liposome Technology* Vol. II, ed G. Gregoriadis CRC Press, Boca Raton, Fla.

E. Therapeutic Methods

The polypeptides, conjugates and compositions contemplated by the present invention are useful as agents for modulating those physiologic events induced by native apo E, such as immune response, steroidogenesis and/or enhance hepatic LDL-binding. For instance, a polypeptide and/or conjugate of this invention can be used as an immunosuppressive agent to inhibit the proliferation of lymphocytes or as an agent to inhibit ovarian androgen production. The polypeptide and/or conjugate is administered to the animal, such as a human, in need of such treatment, in a predetermined amount calculated to achieve the desired effect, i.e., in a therapeutically effective amount.

For instance, when used as an immunosuppressive agent for inhibiting lymphocyte proliferation, such as in a patient displaying the symptoms of an autoimmune disease, the polypeptide and/or conjugate is administered in an amount sufficient to achieve a plasma concentration of at least about 0.8 ug/ml, preferably at least about 1.0 ug/ml, more preferably at least about 2 ug/ml, and usually 3 or 4 ug/ml.

In some cases, it is desirable to apply the subject polypeptide and/or conjugate locally as an immunosuppressive agent. For instance, about 10 ug to about 1 mg can be applied by injection into an arthritic joint (e.g., into the synovial fluid of the joint) to suppress inflammation.

When used as an agent for inhibiting ovarian androgen production, such as in females having polycystic ovaries, the polypeptide and/or conjugate of this invention is administered in an amount sufficient to achieve a plasma concentration of at least about a 2 ug/ml, preferably about 5 ug/ml, and more preferably about 10 ug/ml.

When the tandem apo E peptide $p(141-155)_2$ or its self conjugate is used to inhibit lymphocyte proliferation, the peptide or its conjugate is administered in an amount sufficient to achieve a plasma concentration of at least about 8 mg/ml, preferably at least 10 mg/ml, and more preferably at least 15 mg/ml. When used to enhance lymphocyte proliferation, the peptide or its conjugate is given in an amount sufficient to achieve a plasma concentration of from about 2 mg/ml to about 6 mg/ml, preferably from about 3 mg/ml to about 5 mg/ml.

When the tandem apo E peptide $p(141-155)_2$ or its self conjugate is used to inhibit ovarian androgen production, the peptide or its conjugate is administered in an amount sufficient to achieve a plasma concentration of at least about 0.6 mg/ml, preferably at least 1.0 mg/ml, and more preferably at least 8 mg/ml. When used to enhance ovarian androgen production, the peptide or its conjugate is given in an amount sufficient to achieve a plasma concentration of from about 0.1 mg/ml to about 0.4 mg/ml, preferably from about 0.2 mg/ml to about 0.3 mg/ml.

When a composition contains either tandem apo E peptide $p(141-155)_2$ or its self conjugate operatively linked to an LDL binding moiety is used to enhance hepatic LDL binding and uptake, as in subjects with hyper-cholesterolemia, the composition is administered in an amount sufficient to achieve a tandem peptide or conjugate plasma concentration of at least about 20 mg/ml, preferably at least about 50 mg/ml, and more preferably at least about 100 mg/ml.

The preparation of therapeutic compositions which contain polypeptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients lo which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-containing compositions are conventionally administered intravenously or at the site of autoimmune-induced inflammation, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition of lymphoproliferation or androgen production desired. Precise amounts of active ingredient required to be administered depend on the judgment of the practitioner and are peculiar to each individual. However, suitable dosage ranges for systemic application are of the order of 0.01 to 10, preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

F. Antibodies and Monoclonal Antibodies

The term "antibody" in its Various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', $F(ab')_2$ and F(v).

Fab and $F(ab')_2$ portions of antibodies are prepared by the proteolytic reaction of papain and pepsin, respectively, on substantially intact antibodies by methods that are well known. See, for example, U.S. Pat. No. 4,342,566 to Theofilopolous and Dixon. Fab' antibody portions are also well known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

An antibody of the present invention, i.e., an anti-apo E antibody, in one embodiment is characterized as being capable of immunoreacting with apo E present on cholesterol containing-lipoprotein particles such as LDL, VLDL and the like. Apo E in association with VLDL is referred to as apo E/VLDL. An anti-apo E antibody of this embodiment is further characterized as immunoreacting with the polypeptide of this invention comprising a plurality of segments having the formula p(141-155), preferably $p(141-155)_2$, more preferably $p(141-155)_3$, and still more preferably self-conjugates of $p(141-155)_2$ or $p(141-155)_3$.

In a preferred embodiment, an anti-apo E antibody is characterized as being substantially free of antibody molecules that immunoreact with the polypeptide LSKELQAAQARLGADMEDVR corresponding to residues 93-112 of mature apo E and designated p93-112, or with the polypeptide RGLSAIRERL corresponding to residues 172-182 of mature apo E and designated p172-182.

Particularly preferred are antibody molecules that do not immunoreact with a polypeptide containing only a monomer of the apo E polypeptide p141-155. Apo E polypeptides that contain only a single p141-155, do not have the capacity to mimic the LDL receptor-binding capacity of apo E that results in enhanced hepatic uptake and degradation of apo E-containing lipoprotein particles as disclosed herein. Polypeptides that mimic the LDL receptor binding function of apo E are referred to as "receptor-competent" apo E polypeptides. Anti-apo E antibody molecules that do not immunoreact with monomeric p141-155 thus have immunospecificity for receptor-competent apo E polypeptides, and have immunospecificity for apo E apolipoprotein that is in a receptor-competent form.

Anti-apo E antibody molecules that are specific for receptor-competent apo E or apo E polypeptides have a particular utility in immunoassays, namely, to monitor the fate of therapeutically administered apo E polypeptides during the course of therapeutic regimens as disclosed herein, or to detect the levels of receptor-competent apo E in a vascular body fluid sample.

Antibody immunoreactivity with apo E-containing antigens can be measured by a variety of immunological assays known in the art. Exemplary immunoreaction of an anti-apo E antibody of this invention by direct binding with apo E/VLDL or with apo E polypeptides can be assayed at least by the methods described in Example 8.

An antibody of the present invention is typically produced by immunizing a mammal with an inoculum containing an apo E polypeptide of this invention, such as a self-conjugate of $p(141-155)_3$, and thereby inducing in the mammal antibody molecules having immunospecificity for apo E polypeptide. Alternatively, apo E/LDL or apo E/VLDL can be used as the source of immunizing apo E antigen. Exemplary are the production methods for preparing a polyclonal anti-apo E polypeptide antisera described in Example 8. The antibody molecules are then collected from the mammal and isolated to the extent desired by well known techniques such as, for example, by using DEAE Sephadex to obtain the IgG fraction.

To enhance the antibody specificity, antibodies that are purified by immunoaffinity chromatography using solid phase-affixed immunizing polypeptide are preferred. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

In a related method to produce an anti-apo E antibody that does not substantially immunoreact with monomeric p141-155, the prepared anti-apo E antibody can be contacted with solid-phase monomeric p141-155 so as to allow antibodies that immunoreact with monomeric p141-155 to complex in the solid phase, and the liquid-phase antibody is then collected to form anti-apo E antibody that is specific for receptor-competent apo E polypeptides.

The antibody so produced can be used, inter alia, in the diagnostic methods and systems of the present invention to detect apo E or apo E polypeptide present in a body sample.

The word "inoculum" in its various grammatical forms is used herein to describe a composition containing a apo E polypeptide of this invention as an active ingredient used for the preparation of antibodies immunoreactive with an apo E polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein, et al., *J. Infect. Dis.*, 147:318-326 (1983) and the like, or the use of carbodiimide technology as in the use of a water-soluble carbodiimide to form amide links to the carrier. For a review of protein conjugation or coupling through activated functional groups, see Avrameas, et al., *Scand. J. Immunol.*, 1:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine; D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Avrameas, et al., *Scand. J. Immunol.*, Vol. 8, Suppl. 7:7-23 (1978) and U.S. Pat. Nos. 4,493,795, 3,791,932 and 3,839,153. In addition, a site directed coupling reaction can be Carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

A particularly preferred anti-apo E antibody is a monoclonal antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

Preferred anti-apo E monoclonal antibodies are prepared as disclosed herein.

Additional monoclonal antibodies useful for practicing the diagnostic methods of this invention are those which immunoreact with LDL, VLDL, HDL, and the like lipoprotein particles. Particularly preferred are anti-apo B-100 antibodies.

An exemplary hybridoma that secretes monoclonal antibody molecules that immunoreact with apo B-100 has been described previously in U.S. Pat. No. 4,677,057, which is incorporated herein by reference, and the monoclonal antibody molecules secreted by the hybridoma are referred to herein as MB47. The MB47 monoclonal antibody immunoreacts with more than about 90 percent of $^{125}$I-LDL, and with a distinct and separate conserved antigenic determinant on apo B-100. As pointed out in Young et al. (1986) *Clin. Chem.*, 32/8:1484–1490, MB47 reacts only with apo B-100.

The above hybridoma was deposited with the American Type Culture Collection (ATCC), Rockville, Md., in accordance with the Budapest Treaty on the International Recognition of the Deposit of Microorganisms for the Purposes of Patent Procedure, on Mar. 6, 1985, and was assigned the designation HB 8746.

The above deposit was made in compliance with the Budapest Treaty requirements that the duration of the deposit or for 5 years after the last request for the deposit at the depository or for the enforceable life of a U.S. patent that matures from this application, whichever is longer. The hybridoma is replenished should it become non-viable at the depository, and is made available to the public by the ATCC upon the issuance of a patent from this application.

G. Preparation of Monoclonal Antibodies

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. The preparation of such antibodies was first described by Kohler and Milstein, *Nature*, 256:495–497 (1975), which description is incorporated by reference. The hybridoma supernates so prepared can be screened for the presence of antibody molecules that immunoreact with an apo E polypeptide of this invention.

Briefly, to form the hybridoma from which the monoclonal antibody composition is produced, a myeloma or other self-perpetuating cell line is fused with lymphocytes obtained from the spleen of a mammal hyperimmunized with an apo E polypeptide of this invention, or with a native apo E molecule, such as is present in an apo E-containing lipoprotein particle. The polypeptide-induced hybridoma technology is described by Niman, et al., *Proc. Natl. Sci., U.S.A.*, 80:4949–4953 (1983), which description is incorporated herein by reference.

It is preferred that the myeloma cell line used to prepare a hybridoma be from the same species as the lymphocytes. Typically, a mouse of the strain 129 G1X$^+$ is the preferred mammal. Suitable mouse myelomas for use in the present invention include the hypoxanthine-aminoptorin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are then identified by screening for the immunospecificities of an anti-apo E antibody as disclosed herein, for example, the enzyme linked immunosorbent assay (ELISA) described in Example 10, or using the solid phase radioimmunoassay (SPRIA) described in Example 8.

A monoclonal antibody of the present invention can also be produced by initiating a monoclonal hybridoma culture comprising a nutrient medium containing a hybridoma that secretes antibody molecules of the appropriate immunospecificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice, and the like. An exemplary synthetic medium is Dulbecco's minimal essential medium (DMEM; Dulbecco, et al., *Virol.*, 8:396 (1959)) supplemented with 4.5 gm/l glucose, 20 mm glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci.*, 86:5728–5732 (1989); and Huse, et al., *Science*, 246:1275–1281 (1981).

Also contemplated by this invention is the hybridoma cell, and cultures containing a hybridoma cell that produce a monoclonal antibody of this invention.

The monoclonal antibody produced by the above method can be used, for example, in diagnostic modalities disclosed herein where formation of an apo E-containing immunoreaction product is desired.

Hybridoma HB 8746 produces MB47 monoclonal antibody molecules and was formed by fusing splenocytes of mice immunized with LDL and P3X63Ag8.653.1 myeloma cells. Detailed preparation of the MB47 monoclonal antibody and hybridoma was reported by Young, et al. (1986) *Arteriosclerosis*, 6:178–188.

H. Assay Methods

Useful solid and liquid phase assay methods are discussed herein. However, the invention is not so limited. Further, while the particularly described assay methods utilize an enzyme-linked indicator means, the present invention is not specifically limited to such assays. Additional assay methods are described hereinbelow with particular emphasis on solid phase immunoassay methods.

Those skilled in the art will understand that there are numerous methods of solid phase immunoassays that may be utilized herein. Exemplary, useful solid phase assays include enzyme multiplied immonoassay techniques (EMIT) and flourescence immune assays (FIA), in addition to the specifically discussed RIA, solid phase radioimmunoassay (SPRIA) of Example 8B, and ELISA. However, any method that results in a signal imparted by the reaction of apo E with an antibody of this invention is considered. Each of those assay methods can employ single or double antibody techniques in which an indicating means is utilized to signal the immunoreaction, and thereby the binding of an apo E that is to be assayed with a receptor of this invention. Exemplary techniques can be found explained in Maggio, *Enzyme Immunoassay,* CRC Press, Cleveland, Ohio (1981); and in Goldman, *Fluorescent Antibody Methods,* Academic Press, New York, N.Y. (1980).

A vascular fluid sample is utilized in this assay method. The sample can be either serum or plasma. Results obtained using both compositions have previously been found to be statistically indistinguishable. Regardless of whether serum or plasma is used, the vascular fluid sample is preferably obtained from persons who have fasted for at least about twelve hours as is known in the art. Such a blood sample is referred to as a "fasting" sample.

One contemplated assay method determining the presence, and preferably the amount of an apo E in a vascular fluid sample. This method includes the following steps.

(a) A vascular fluid sample is admixed with an anti-apo E antibody composition to form an immunoreaction admixture. The antibody molecules in the composition preferably are operatively linked to a solid support such that the immunoreaction admixture has both a liquid phase and a solid phase. These antibody molecules immunoreact with:

(1) a polypeptide containing a plurality of segments each having an amino acid residue sequence corresponding to the formula:

Leu—Arg—Lys—Leu—Arg—Lys—
Arg—Leu—Leu—Arg—Asp—Ala—Asp—Asp—
Leu. and (2) apo E/VLDL, but do not immunoreact with a polypeptide corresponding to one of the formulae p93-112 and p172-182, and preferably do not immunoreact with a polypeptide containing only a monomer of the polypeptide p141-185.

(b) The immunoreaction admixture is maintained under biological assay conditions for a time period sufficient to form an apo E-containing immunoreaction product in the solid phase.

(c) The presence, and preferably the amount of immunoreaction product formed in step (b) and thereby apo E antigen in the vascular fluid sample is then determined.

Biological assay conditions are those conditions that are able to sustain the biological activity of the immunochemical reagents of this invention and the antigen sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

In a preferred embodiment of the above method the amount of immunoreaction product is determined according to step (c) by (i) admixing a labeled specific binding agent capable of binding an apo E-containing particle with the apo E-containing immunoreaction product to form a labeling reaction admixture, (ii) maintaining the labeling reaction admixture under biological assay conditions for a time period sufficient for the labeled specific binding agent to bind the apo E-containing immunoreaction product to form a labeled complex, and (iii) detecting the amount of any labeled complex formed, and thereby detecting the amount of apo E-containing immunoreaction product.

In a particularly preferred embodiment, the labeled specific agent is a monoclonal anti-B-100 antibody produced by the hybridoma having ATCC designation HB 8742.

Another contemplated assay of this invention is a method for detecting the presence, and preferably the amount of an apo E antigen in a vascular fluid sample. This assay method comprises the following steps.

A vascular fluid sample is admixed with a solid phase-bound apo E peptide containing a plurality of segments each having an amino acid residue sequence corresponding to the formula Leu—Arg—Lys—Leu—Arg—Lys—
Arg—Leu—Leu—Arg—Asp—Ala—Asp—Asp—
Leu to form a first solid-liquid phase admixture.

An antibody composition, containing a limiting amount of anti-apo E peptide antibody molecules that immunoreact with (i) a polypeptide containing a plurality of segments each having an amino acid residue sequence corresponding to the formula Leu—Arg—Lys—Leu—Arg—Lys—
Arg—Leu—Leu—Arg—Asp—Ala—Asp—Asp—
Leu. and (ii) apo E/VLDL, but do not immunoreact with a polypeptide corresponding to one of the formulae p93-119 and p72-182, and preferably do not immunoreact with a polypeptide containing only a monomer of the polypeptide p141-155, is admixed with the first admixture to form a second admixture.

This second admixture is maintained under biological assay conditions for a period of time sufficient to form an apo E-containing immunoreaction product in the solid phase. The amount of immunoreaction product present in the solid phase formed in step (c) is determined, and thereby the amount of apo E in the vascular fluid sample.

In an alternative embodiment, the solid phase-bound apo E polypeptide is replaced by an apo E-containing lipoprotein, such as a VLDL particle.

In a more preferred embodiment, the solid phase-bound apo E polypeptide or apo E containing component is the above-described receptor-competent polypeptide analog, and the anti-apo E analog antibody in step (b) is operatively linked to an enzyme indicating means, and the product formed in step (c) is a labeled immunoreaction product.

Insofar as the present diagnostic methods can be used to monitor the fate of therapeutically administered apo E polypeptides as disclosed herein, it is understood that the disclosed methods for detecting an apo E antigen can readily be applied to monitor an analog of an apo E antigen, namely, an apo E polypeptide. For this reason, the phrase "apo E antigen" refers to antigenic molecules that immunoreact with the antibodies of the present invention, whether the antigenic molecules are native apo E, apo E polypeptides, or combinations of both analog and native protein.

In embodiments for following the fate of a therapeutically administered apo E polypeptide, it is to be understood that native apo E and apo E polypeptide may be indistinguishable in a vascular fluid sample where both components immunoreact with the anti-apo E antibodies. Therefore, it is useful and preferred to measure vascular levels of apo E antigen in a patient prior to the administration of a therapeutic composition to establish a baseline of apo E antigen in the patient. At predetermined time intervals after administration of therapeutic peptide, the patient's blood is then sampled and the levels of apo E antigen are again measured to determine the effect and fate of the therapeutic composition on circulating apo E antigen.

Also contemplated is a related method for detecting apo E present in lipoprotein particles in a vascular fluid sample. The fluid sample is admixed with a solid-phase anti-B-100 antibody, i.e., operatively linked to a solid matrix, to form a liquid-solid phase immunoreaction admixture. The admixture is maintained under biological assay conditions for a time period sufficient to form an immunoreaction product in the solid phase. The immunoreaction product, containing lipoprotein particles with apo B-100, is then admixed with an anti-apo E antibody of this invention to form a second liquid-solid phase immunoreaction admixture. The second admixture is maintained as before to allow the anti-apo E antibodies to immunoreact with the solid-phase lipoprotein particles and form a second solid-phase immunoreaction product. The resulting second product is detected to indicate the presence of apo E in the vascular fluid.

In preferred embodiments, the anti-apo E is labeled, and the second product is thereby detected by detecting the presence of label in the solid phase. More preferably, the anti-apo E antibody has the capacity to bind receptor-competent apo E polypeptides, and can therefore be useful to determine receptor-competent apo E rather than total apo E.

Techniques for operatively linking an enzyme to an antibody molecule to form a conjugate are well known in the art. Exemplary techniques are discussed in Maggio, *Enzyme-Immunoassay,* Chapter 4 by Kabakoff, CRC Press, Boca Raton, Fla. (1980), pages 71–104.

The monoclonal antibody molecules can be utilized as obtained from hybridoma supernatants or as ascites. However, it is preferred that purified monoclonal antibody molecules be utilized.

Several means for purification of monoclonal antibody molecules are well known in the art and typically utilize chromatographic techniques. Fast protein liquid chromatography (FPLC) is the purification technique of choice herein.

The enzyme-linked monoclonal antibody molecule conjugates are provided to the admixtures in the fluid phase. Those molecules are typically dissolved in an aqueous composition. Typical compositions contain buffer salts as is the case of the exemplary purified monoclonal antibody-containing compositions used herein that include phosphate-buffered saline (PBS) as a diluent. Diluted ascites fluid also is useful.

Preferably, non-specific protein binding sites on the surface of the solid phase support are blocked. Thus, the solid phase-bound paratopic molecules are bound as by adsorption or other well known means of affixation to the solid matrix. Thereafter, an aqueous solution of a protein free from interference with the assay such as bovine, horse or other serum albumin that also is free from contamination with human apo B-100 or apo E is admixed with the solid phase to adsorb the admixed protein onto the surface of the paratopic molecule-containing solid support at protein binding sites on the surface that are not occupied by the monoclonal paratopic molecule.

A typical aqueous protein solution contains about 3 to about 10 weight percent bovine serum albumin in PBS at a pH value of 7.1–7.5. The aqueous protein solution-solid support admixture is typically maintained for a time period of at least one hour at 37 degrees C., and the resulting solid phase is thereafter rinsed free of unbound protein.

The vascular fluid sample can be plasma or serum, as already noted. The sample is preferably diluted at about 1:500 to about 1:5000, and more preferably at about 1:1000. The use of lesser dilution can provide too much of the apolipoprotein antigen to the admixture and impair the linearity of the assay results as well as lower or abolish the solid phase-bound paratopic molecule excess over the admixed antigen. Use of greater than about a 1:20,000 dilution tends to decrease precision.

The maintenance times utilized can vary widely with little variance in result so long as a minimum time of about 30 minutes at ambient room temperature (about 20–25 degrees C.) is utilized. Where it is desired to use a minimum 30-minute maintenance time, it is preferred that the maintained admixture be agitated during that time period to assure substantially complete immunoreaction between the apolipoprotein antigen and monoclonal paratopic molecules. Where longer maintenance times such as one hour or more at room temperature are utilized, agitation typically is not required. The desired agitation can be readily supplied by means of a gyroshaker operated at about 100 rpm. Each of the assays used in the method is capable of being carried out using immunoreaction admixture maintenance times of about 30 minutes to about 60 minutes at ambient room temperatures.

The amount of apolipoprotein antigen present in the assayed immunoreactant is determined by admixture of the separated enzyme-linked apolipoprotein-containing solid phase with a predetermined amount of visualizing reagent or reagents. Where HRPO is utilized as the enzyme indicating means, visualizing reagents such as hydrogen peroxide and an oxidative dye precursor such as o-phenylenediamine (OPD) present in an aqueous medium are admixed with the separated solid phase-bound immunoreactant. The admixture so formed is maintained under biological assay conditions for a predetermined time such as at least about 30 minutes at ambient temperature for color to develop. Color development is thereafter stopped by admixture of a stopping reagent such as sulfuric acid. The optical density of the composition is thereafter read, compared to a standard curve value, and the amount of apolipoprotein is determined, as is well known.

Thus, once the solid support and vascular fluid sample are prepared, each assay can be carried out at ambient room temperature in a time period of about one hour; i.e., a 30-minute maintenance time with agitation for admixtures formed from both paratopic molecules and the sample aliquot, and another 30-minute maintenance time for color development. Indeed, one need not prepare the solid support just prior to each use, but rather, such supports as are described herein can be prepared and stored damp and covered under usual refrigeration conditions for a period of at least one month prior to use.

G. Diagnostic Systems

The present invention also contemplates a diagnostic system, typically in kit form, that can be utilized in carrying out the before-described assay methods. The system includes, in an amount sufficient for at least one assay, a subject apo E polypeptide and/or anti-apo E antibody or monoclonal antibody of this invention as separately packaged immunochemical reagents. Instructions for use of the packaged reagent are also typically included.

In one embodiment, a diagnostic system in kit form includes a solid support comprising a solid matrix such as a microtiter plate having an anti apo-E monoclonal antibody of this invention affixed thereto (operatively linked to the solid matrix) in an amount sufficient to carry out at least one assay.

In preferred embodiments, the above diagnostic system further includes, as a separately packaged reagent, a second antibody, a reveal antibody, that contains antibody molecules that immunoreact with apo E-containing lipoprotein particles. In this embodiment, the reveal antibody can immunoreact with any component present on the apo E-containing lipoprotein particle. Such particles include apo E/LDL, apo E/VLDL, apo E/HDL, and the like. Preferred are reveal antibodies that immunoreact with apo B-100 because it is a conserved epitope on apo E-containing lipoprotein particles. Particularly useful anti B-100 antibody molecules are the monoclonal antibodies secreted by the hybridomas MB47, which is available from the ATCC and has the accession number HB8746.

In another embodiment used for assaying a fluid sample for the presence of apo E polypeptide or apo E-containing lipoprotein particles, a diagnostic system includes a solid support comprising a solid matrix having affixed thereto an apo E polypeptide of this invention. The system can further include, as a separately packaged reagent, an anti-apo E polypeptide antibody of this invention for use in a competition ELISA format.

Preferably, a diagnostic system further includes one or more of the following: (i) a supply of hydrogen peroxide of known concentration; (ii) a visualizing oxidative dye precursor such as OPD; (iii) a solution of a stopping agent such as 4N sulfuric acid to quench the color-forming reaction; (iv) one or more buffers in dry or liquid form for use in the assay; and (v) materials for preparing standard reference curves.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium of $^{3}H$.

The linking of labels, i.e., labeling, of polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Aurameas, et al., *Scand. J. Immunol.,* Vol. 8 Suppl. 7:7-23 (1978), Rodwell et al., *Biotech.,* 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of apo E in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

A reagent is typically affixed to a solid matrix by adsorption from an aqueous medium although other modes of affixation applicable to proteins and polypeptides well known to those skilled in the art, can be used.

Thus, in preferred embodiments, an apo E polypeptide, or anti-apo E antibody molecule, of the present invention can be affixed in a solid matrix to form a solid support that comprises a package in the subject diagnostic system.

Useful solid matrices are also well known in the art for preparing a solid support containing a reagent affixed thereto. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

I. EXAMPLES

The following examples are intended to illustrate, but not limit, the present invention.

1. Polypeptide And Conjugate Preparation a. Synthesis

The polypeptides p(141-155)$_2$, referred to as "tandem peptide", p(141-155)$_3$, and other disclosed polypeptides were synthesized using the classical solid-phase technique described by Merrifield, *Adv. Enzymol.*, 32:221-96, (1969) as adapted for use with a model 430A automated peptide synthesizer (Applied Biosystems, Foster City, Calif.). Polypeptide resins were cleaved by hydrogen fluoride, extracted and analyzed for purity by high-performance liquid chromatography (HPLC) using a reverse-phase C18 column manufactured by Waters Associates, Milford, Mass.

b. Self-Conjugation of Apo E Peptides p141-155 and p129-163

The synthetic peptides containing the amino acid residues 141-155 or 129-163 of apo E or the peptide p(141-155)$_2$ were self-conjugated (i.e., p141-155 was coupled to p141-155 and p129-163 Was coupled to p129-163) according to the procedure of Hoare et al., *J. Biol. Chem.,* 242:2447, (1967). Briefly, 100 mg of synthetic peptide was dissolved in 10 ml of high purity water (Nanopure system). One gram of EDG [1-ethyl-3-(3-dimethylaminopropyl) carbodiimide hydrochloride] was admixed to the peptide solution. The reaction proceeds rapidly at room temperature and is complete after one hour. During the first five to ten minutes the pH of the reaction admixture is monitored. The starting solution, before the addition of EDG, is at a pH of approximately 3.7. Upon the addition of EDG, the pH increases to approximately 5.0 in the first five minutes. At five minutes, 50 ul of 0.1N HCL is added. No further addition of acid is necessary during the rest of the incubation. The admixture is rotated while incubating to insure complete reaction. The reaction is quenched with 10 ml of 2M acetate buffer, pH 4.75.

To isolate conjugated (operatively linked) peptides from unreacted peptide and chemicals, the self-conjugation preparation is dialyzed in 2,000 molecular weight cut-off dialysis tubing, 18 millimeter wide and approximately two times the length of the sample volume. Starting dialysis is done against 2M acetic acid. A gradient reducing the concentration of acetic acid from 2M to <0.01M is achieved by changing the dialysis buffer (one liter) every hour stepping down the concentration of acetic acid by 50% at each change. Once the acetic acid concentration has been lowered to <10 mM, the sample is then dialyzed against one liter highly purified water over night at room temperature with at least five one liter changes. The sample is lyophilized to dryness and redissolved in phosphate-buffered saline (PBS) and is ready for addition to cell culture.

The yield of self-conjugated peptide from this procedure is low, usually not greater than 5%. For instance, in one conjugation starting with 100 mg of synthetic peptide, 2.82 mg of p141-155 self-conjugated peptide was recovered. The polypeptide concentration of the peptide redissolved in PBS was determined by the Lowry protein assay method. All additions of peptide to cell culture of this self-conjugated preparation were based on the value from Lowry assay. The activity in the self-conjugated p141-155 preparation is stable for at least two months when stored at −20° C.

2. Apo E polypeptide binds Lipoproteins

To assess the degree of binding of the tandem peptide with lipoproteins, $^{125}$I-tandem peptide was mixed with very low density lipoprotein (VLDL), LDL, high density lipoprotein (HDL) or lipoprotein-depleted serum (LPDS) to measure direct binding. Briefly, the lipoproteins were isolated by ultracentrifugation according to Curtiss, et al., *J. Biol. Chem.,* 257:15213 (1982). The lipoprotein-depleted serum (LPDS) was obtained as the bottom fraction remaining after flotation of the HDL at a density of 1.25 gm/ml. All fractions were diluted in PBS containing 3% bovine serum albumin (BSA). The tandem peptide $p(141-155)_2$ was radiolabeled using the iodine monochloride method of Brown et al., *Methods Enzymol.,* 98:241 (1983) to a specific activity of $7.99\times10^6$ cpm/ug and was 99% precipitable in 10% trichloroacetic acid (TCA). The binding assays were performed in siliconized tubes in a total volume of 0.3 ml of PBS that contained 3% BSA, 20 μg of lipoprotein or LPDS and 250 ng of $^{125}$I-tandem peptide. After 1 hr at 37° C. the lipoprotein bound peptide was separated from the free peptide. Tubes containing VLDL, LDL and LPDS were precipitated with 0.3 ml of 555 uM phosphotungstic acid and 25 mM $MgCl_2$ and tubes containing HDL was precipitated with 0.3 ml of an apo AI-specific antiserum. Each precipitation condition had been previously optimized with the use of radioiodinated lipoproteins and was designed to achieve 100% precipitation of the lipoproteins. Precipitated radioactivity was measured by detecting gamma radiation and expressed based on specific activity as nanograms (ng) of peptide bound per microgram (ug) of protein.

The results, shown in Table 2, indicate that less than 0.7% of the added $^{125}$I-tandem peptide was associated with HDL, and that 58% and 39% of the added peptide was found associated with VLDL and LDL, respectively. Calculated as the number of tandem peptide molecules bound per lipoprotein particle, VLDL, LDL and HDL each contained 1.8, 0.25 and 0.0043 peptide molecules per particle, respectively. Therefore, the apo E polypeptide $p(141-155)_2$ preferentially binds lipoprotein particles in the following order VLDL>LDL>HDL.

TABLE 2

| LIPOPROTEIN OR PROTEIN | ng of $^{125}$I-tandem peptide bound per μg protein | Molar ratio of peptide per lipoprotein particle |
|---|---|---|
| VLDL | 7.25 | 1.8 |
| LDL | 1.87 | 0.25 |
| HDL | 0.07 | 0.0043 |
| LPDS | 0.76 | — |

3. A Tandem Peptide Affects LDL Binding and Degradation

The LDL receptor binding properties of the tandem peptide were assessed using normal human fibroblasts and a transformed human monocytic-like cell line, THP-1 as a source of LDL receptor. THP-1 cells were studied because both the LDL receptor and another lipoprotein receptor, the scavenger receptor, are present and binding with those receptors is easily examined. In the undifferentiated state THP-1 cells express LDL receptors that are regulated by the lipoprotein content of the culture medium; Hara, et al., *Biochem. Biophys. Res. Commun.,* 146:802 (1987); Via, et al., *J. Lipid Res.,* 30:1515 (1989). Following phorbol myristate acetate ester (PMA)-stimulation the cells stop dividing, differentiate into macrophage-like cells, eventually lose most of their LDL receptors and acquire scavenger receptors that bind acetylated or modified LDL; Hara, et al., *Biochem. Biophys. Res. Commun.,* 146:802 (1987); Via, et al., *J. Lipid Res.,* 30:1515 (1989).

a. Inhibition of degradation by unstimulated THP-1 cells

THP-1 cells were acquired from American Type Culture Collection and cultured in serum-free RPMI-1640 medium supplemented with 1% Nutridoma-HU for 48 hr to upregulate the LDL receptors. LDL was isolated by ultracentrifugation and radiolabeled using the iodine monochloride method as described in Example 2 to a specific activity 200-300 cpm/ng. Greater than 99% of the $^{125}$I-LDL ligand was precipitable by 10% TCA. The peptides indicated in FIG. 1 were synthesized, as described in Example 1, purified to >95% by high pressure liquid chromatography and the amino acid composition verified. All peptides were solubilized in PBS.

Binding and degradation of LDL was evaluated as the disappearance of acid soluble $^{125}$I-LDL radioactivity from the incubation over a 5-hour incubation at 37° C. Various concentrations of unlabeled LDL or tandem apo E peptide were coincubated with the $^{125}$I-LDL to determine their effects on binding and degradation.

For assay, $5\times10^5$ THP-1 cells in 0.5 ml DMEM were incubated in a 1.5 ml microfuge tube with 2-5 μg/ml of $^{125}$I-LDL at 37° C. After 5 hr the cells were pelleted at 5000×g and the supernatants were removed and extracted with 10% TCA. The results were expressed as B/Bo where B−TCA soluble cpm in presence of LDL or peptide and $B_o$−TCA soluble cpm in phosphate buffered saline (PBS) control cells. Each point is the average of 4 replicates with standard error of the mean (SEM), 10%.

As shown in FIG. 1 (top panel), the tandem 141-155 apo E peptide enhanced LDL degradation by unstimulated THP-1 cells at low concentrations and inhibited LDL degradation at high concentrations. In this experiment, enhancement of LDL concentration occurred at tandem apo E peptide concentrations ranging from about 0.08 to about 1.5 μM. Inhibition of LDL degradation began to occur at tandem apo E peptide levels of 2.0 to 5.0 μM. Unlabeled LDL inhibited $^{125}$I-LDL degradation, indicating the specificity of the LDL receptor. It can be seen that neither a control apo A-I 74-105 peptide or the monomer apo E 141-155 peptide LDL inhibited $^{125}$ degradation. In contrast, the tandem apo E peptide inhibited $^{125}$I-LDL degradation by 50% at 5 uM. Approximately a 200-fold molar excess of the tandem apo E peptide compared with LDL was required to achieve 50% inhibition of degradation.

b. Inhibition is LDL receptor-specific

To verify that the inhibition of LDL degradation was specific for the LDL receptor, the effect of the tandem peptide on scavenger receptor processing of acetylated LDL (aLDL) was tested.

THP-1 cells ($5\times10^5$ in 1.0 ml of DMEM medium per 16 mm culture dish) were stimulated with PMA ($10^{-7}$M) for 4 days. LDL was acetylated (Hara, H. et al., *Biochem. Biophys. Res. Comm.*, 146(2):802–808, 1987) and then radio-labeled as described in Example 2 to a specific activity of 300–500 cpm/ng resulting in $^{125}$I-LDL that was greater than 99% precipitable by 10% TCA. The cells were washed with PBS and the assay performed in DMEM medium supplemented with 1% Nutridoma-HU plus 25 μg/ml of $^{125}$I-aLDL. After 5 hr at 37° C., the supernatants were removed from the wells and extracted with 10% TCA. The $B/B_o$ ratios were analyzed as described above. The results are depicted in FIG. 1 (bottom panel).

Neither LDL nor the tandem peptide inhibited the degradation of $^{125}$I-aLDL by PMA-stimulated THP-1 cells. As can be seen in FIG. 1 (bottom panel), at 12.5 uM the tandem apo E peptide caused an 80% inhibition of $^{125}$I-LDL degradation but had no effect on $^{125}$I-aLDL degradation.

4. Confirmation of binding by the LDL receptor and Identification of critical amino acids The role of specific amino acids within residues 141–155 of intact apo E has been studied by Lalazar et al., *J. Biol. Chem.*, 263:3542 (1988) with human apo E variants containing single amino acid substitutions. The variants were produced in a bacterial expression system complexed with the phospholipid, dimyristoylphosphatidylcholine (DMPC) and tested for their ability to bind to fibroblast LDL receptors. Lalazar et al., *J. Biol. Chem.*, 263:3542 (1988). To confirm that the tandem peptide was bound by the LDL receptor and to identify amino acids Within this peptide that were critical for binding, three tandem peptides were prepared as described in Example 1 that contained the same amino acid substitutions at both positions in the tandem sequence. The changes included substitutions of the basic amino acids Lys 143 to Ala, Arg 150 to Ala, and Leu 144 with an alpha helix disrupting amino acid, Pro. $^{125}$I-LDL at a specific activity of 700–900 cpm/ng (>99% precipitable by 10% TCA) was used for the binding assay as described in Example 3. Normal fibroblasts were plated in 16 mm culture dishes, grown for 72–96 hr in DMEM medium with 10% fetal bovine serum (FBS) and then transferred to DMEM medium with 10% lipoprotein-depleted serum (LPDS) for 48 hr to upregulate the LDL receptors. The amount of $^{125}$I-LDL bound per well was normalized to the protein content of each well, which was measured with the Bio-Rad protein assay reagent using bovine serum albumin (BSA) as a standard.

As illustrated in FIG. 2, each of the substitutions in $p(141-155)_2$ reduced the ability of the tandem peptide to inhibit the binding of $^{125}$I-LDL to fibroblasts. The Lys 143 to Ala substitution had the smallest effect, whereas the Leu 144 to Pro substitution had the greatest impact. In fact, the Leu 144 to Pro substituted tandem peptide had no activity at 60 uM, an effect that was similar to that observed with the native apo E variant. Lalazar et al., *J. Biol. Chem.*, 263:3542 (1988).

5. Higher ordered multimers of the 141–155 sequence may have greater binding activity.

A trimer of the p141–155 peptide, $p(141-155)_3$, was synthesized as in Example 1 and its activity compared with p(141–155) (monomeric) and with $p(141-155)_2$ (dimeric) peptide. Normal fibroblasts were plated in wells of a 96-well culture plate and grown for 96 hr in DMEM medium with 10% FBS. The cells were transferred to DMEM medium with 10% LPDS for 48 hr to up regulate the LDL receptors. The LDL degradation assay was performed according to Example 3 with 2 μg/ml of $^{125}$I-LDL (300–500 cpm/ng) in 0.2 ml/well in DMEM medium with 10% LPDS and incubated for 5 hr at 37° C. The supernatants removed from the wells were extracted with 10% TCA. The TCA soluble counts were normalized to protein content per well as measured by the Bio-Rad protein assay.

Figure 3:
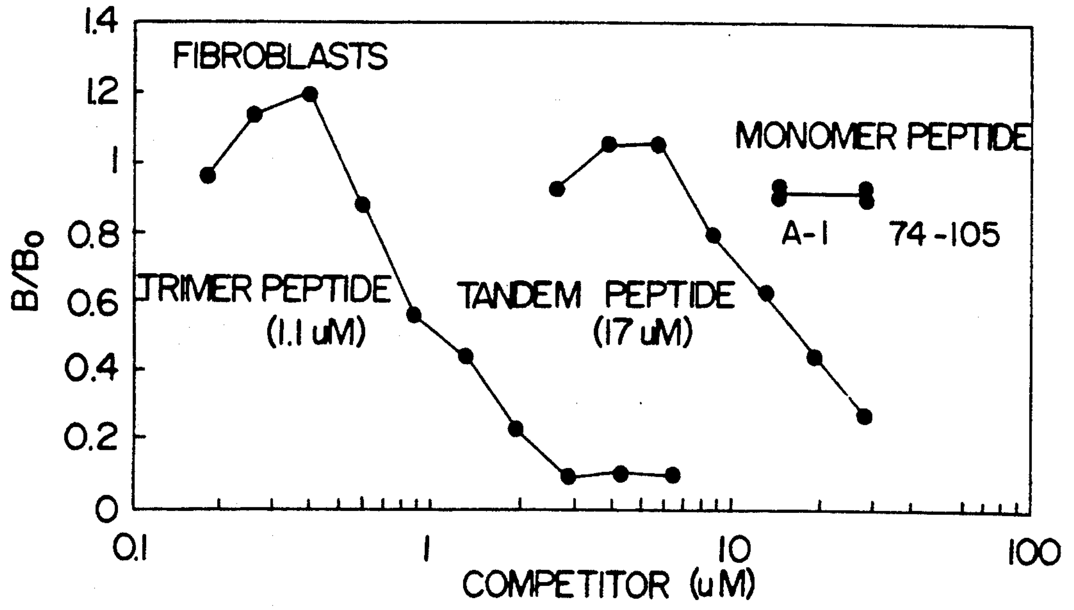
FIG. 3 illustrates that the trimer peptide is a more potent inhibitor of fibroblast LDL degradation than the tandem peptide when assayed as described in Example 5. Each point is the average of 5 replicates per treatment with SEM$<$10%. The results are expressed as $B/B_o$ where B−TCA soluble counts in supernatants from cells treated with peptides divided by $B_o$−TCA soluble counts in supernatants from cells treated with PBS.

Compared on a molar basis for their ability to inhibit fibroblast $^{125}$I-LDL degradation, the trimer peptide was 15 times more effective than the dimeric peptide (FIG. 3). The results indicate that higher ordered multimers of the 141–155 sequence have increased receptor binding activity.

6. Total number of binding sites per cell

The direct binding of the $^{125}$I-tandem peptide to dividing THP-1 cells was measured. THP-1 cells were cultured for 48 hours in LDL-free RPMI-1640 medium containing 1% Nutridoma-Hu. Increasing amounts of $^{125}$I-tandem peptide (17,444 cpm/pmole), labeled as described in Example 2 were added to $5\times10^5$ cells/0.05 ml of DMEM medium containing 1% Nutridoma-Hu combined with 0.05 ml of PBS or 0.05 ml of VLDL 500 μg/ml in siliconized glass tubes. After 20 min at 4° C. the free $^{125}$I-tandem peptide was separated from the bound peptide by sedimenting the cells through silicone oil (29). Background counts were <1000 cpm/tube.

$^{125}$I-tandem peptide binding was found to be linear with cell number, saturable and reached an apparent steady state within 20 min at 4° C. $^{125}$I-tandem peptide binding to THP-1 cells was specifically inhibited by apo B- and apo E-containing lipoproteins with the ability to inhibit ordered as follows:

VLDL>LDL>HDL.

The binding of the $^{125}$I-tandem peptide to the cells also was dependent on $Ca^{++}$. A 2-fold increase in the amount of $^{125}$I-tandem peptide bound to the cells was obtained when the $Ca^{++}$ concentrations were increased from 0.1 to 2.0 mM, whereas $Mg^{++}$ at up to 2.0 mM had no effect. Finally, if THP-1 cells were deprived of LDL-containing serum for 96 hr before $^{125}$I-tandem peptide binding was assayed, a 2–3 fold increase was observed with both ligands, indicating up-regulation of both the LDL receptor and the tandem peptide binding site.

Figure 4A:
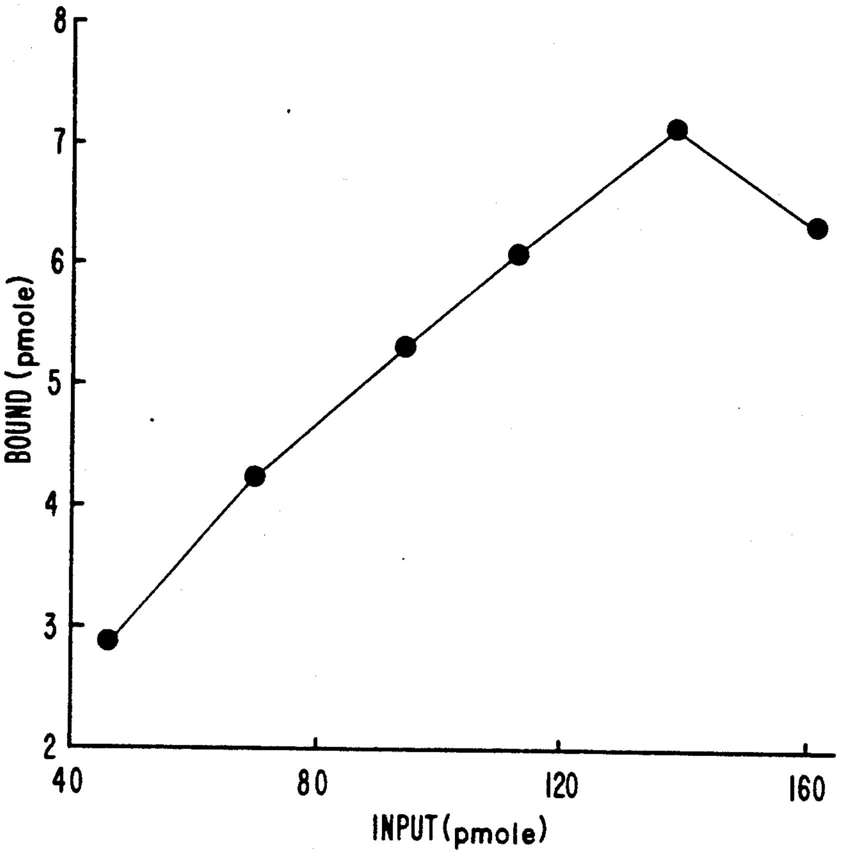
FIG. 4A illustrates a specific, saturable $^{125}$I-tandem peptide binding to THP-1 cells according to the assay described in Example 6. The points shown are the average of 5 replicates (SEM$<$10%) and represent specifically bound pmoles of tandem peptide. The nonspecific binding (i.e. binding in the presence of 500 μg/ml of VLDL) averaged 23.4% of the total counts bound. Scatchard analysis of the data is shown in the figure inset, FIG. 4B.
Figure 4B:
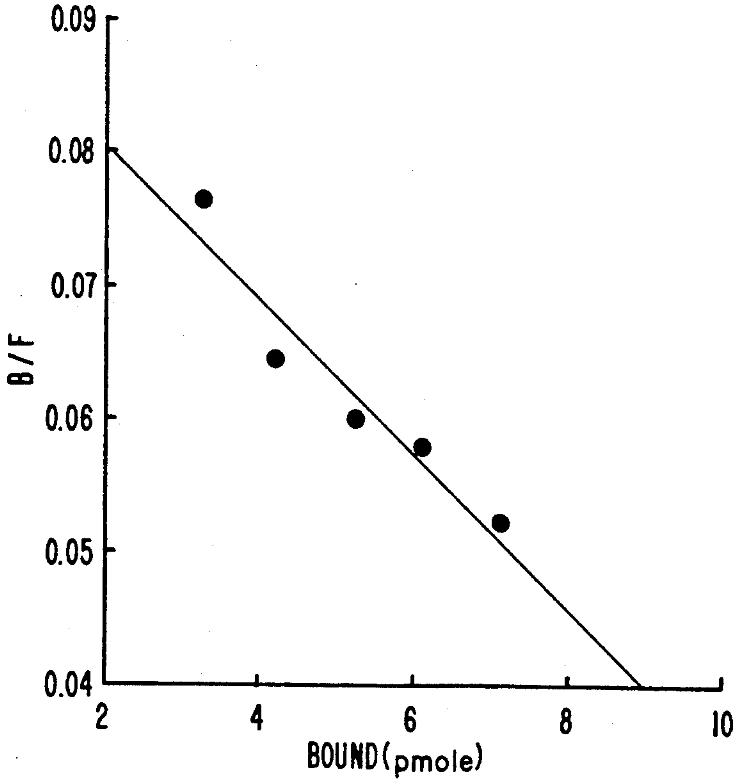

When the binding of the $^{125}$I-tandem peptide to THP-1 cells cultured in LDL-free medium was studied in the presence of 2.0 mM $Ca^{++}$ and in the absence and presence of 500 ug/ml of VLDL, specific saturable binding was observed with a Kd of $1.1\times10^{-7}$M (FIG. 4). From this data the total number of binding sites per cell was calculated to be 1500.

Although the data indicates that the tandem peptide bound the LDL receptor, the LDL receptor may not be the only fibroblast or THP-1 binding site for the tandem peptide. Low density lipoprotein receptor-related protein (LRP) is a recently described cell surface protein that contains reiterated sequences, which are homologous to similar sequences in the LDL receptor; Herz et al., *EMBO J.*, 7:4119 (1988); Beisiegel, et al., *Nature*, 341:162 (1989). Recent studies indicate that LRP may only interact with apo E-enriched lipoproteins including beta-VLDL; Kowal, et al., *Proc. Natl. Acad. Sci. USA*, 86:5810 (1989). Unlike the LDL receptor, the LRP receptor on fibroblasts does not appear to be down regulated by exposure of the cells to LDL; Kowal, et al., *Proc. Natl. Acad. Sci. USA*, 86:5810 (1989).

7. Therapeutic Application

Specific targeting of an apo E polypeptide such as the tandem peptide to cholesterol-rich lipoproteins is accomplished by designing a synthetic peptide that has high affinity lipid and receptor binding properties. Attachment of the 141–155 tandem sequence to a lipophilic molecule or peptide facilitates a specific high affinity association of the tandem sequence with cholesterol-rich lipoproteins and increases the hepatic clearance of the lipoprotein from the circulation. A reproducible and significant enhancement of LDL degradation by THP-1 cells (FIG. 1, top panel) and by fibroblasts (FIG. 3) at low concentrations of the tandem peptide was observed when tandem peptide was contacted with the cells in vitro.

There are several examples cited in the literature in which it has been observed that apo E function is dependent on the number of apo E molecules per lipoprotein particle: (a) reducing the number of apo E molecules per DMPC complex results in decreased binding; Mahley, et al., *Biochim. Biophys. Acta*, 737:197 (1983); (b) VLDL uptake by the liver is enhanced by adding additional copies of thrombin-accessible apo E; Bradley, et al., *J. Biol. Chem.*, 259:14728 (1984); (c) an average of greater than one apo E molecule per particle is required for VLDL to stimulate macrophage cholesterol esterification; Soltys, et al., *J. Lipid Res.*. 29:191 (1988); (d) VLDL carrying more apo E are removed from blood more rapidly; Yamada, et al., *Proc. Natl. Acad. Sci. USA*, 86:665 (1989), and finally (e) only apo E-enriched beta VLDL is taken up by the LRP receptor; Kowal, et al., *Proc. Natl. Acad. Sci. USA*, 86:5810 (1989). It is believed herein that this requirement reflects the close association of at least two copies of apo E to form an LDL receptor-competent apo E ligand.

8. Preparation of Polyclonal Antisera to Synthetic Polypeptides a. Preparation of Immunogen

LDL was isolated from plasma obtained by plasmapheresis of normal pooled rabbit blood (Scripps Clinic and Research Foundation Vivarium, La Jolla, Calif.). Plasma so obtained was adjusted to contain a final concentration of 2 millimolar (mM) benzamidine, 14 mM ethylenediaminetetraacetic acid (disodium salt) (EDTA), 20 micrograms per milliliter (μg/ml) soybean trypsin inhibitor, 10,000 units per ml aprotinin, 20 μg/ml lima bean trypsin inhibitor, 25 μg/ml polybrene, and 1 μM D-phenylalanyl-1-prolyl-1-arginine chloromethyl ketone (PPACK). The LDL was then isolated from this adjusted plasma by sequential ultracentrifugation using solid potassium bromide (KBr) for density adjustment.

First, the adjusted plasma was centrifuged at 186,000×g for 18 to 24 hours at 4 degrees centigrade (4° C.). The top layer of the resulting supernatant containing apo/VLDL was removed and retained. The bottom layer of the supernatant was recovered and admixed with solid KBr layer until the density was greater than 1.063 grams per milliliter (g/ml). The resulting admixture was then layered under a 0.1% EDTA solution containing KBr at density of 1.063 g/ml and centrifuged at 186,000×g for 18 to 24 hours.

After the second centrifugation, the top layer containing LDL was recovered and the bottom layer containing HDL was discarded. The top layer is admixed with solid KBr until the density was adjusted to greater than 1.063 g/ml. That adjusted layer was layered under a 0.1% EDTA solution containing KBr at a density of 1.21 g/ml and was centrifuged at 186,000× g for 18 to 24 hours at 4° C.

The top layer was then recovered, and solid KBr was admixed until the density was greater than 1.063 g/ml. That adjusted top layer was layered under a 0.1% EDTA solution containing KBr at a density of 1.063 g/ml, and still further centrifuged at 250,000×g for 18 to 24 hours at 4° C. The top layer containing concentrated LDL was recovered and dialyzed against PBS (phosphate-buffered saline, pH 7.2) and stored at −70° C.

The multimeric polypeptide analogs of apo E, $(p141–155)_2$, $(p141–155)_3$, and self-conjugates of these, were synthesized as described in Examples 1 and 2. The apo E polypeptide $p(141–155)_2$ was dissolved in 1.5M sodium acetate, pH 7.8, to a final concentration of 6 mg/ml in a total volume of 5 mls. A dissolved polypeptide was admixed with 2.5 ml each of a 2 mg/ml LDL solution and a 3M sodium acetate solution, pH 7.8, for a peptide:LDL ratio of 1000:1. Added to the polypeptide and LDL reaction mixture was a 500 mM glutaraldehyde solution using a 2.7 molar excess of glutaraldehyde to peptide. The admixture was maintained at room temperature for 10 minutes, after which a 40 mM solution of sodium borohydride was added to a final concentration of 0.2 mM. The admixture was thereafter maintained at 37° C. for 5 to 8 hours, followed by dialysis against PBS for 5 days with two buffer changes per day, using dialysis tubing having a 12,000 to 14,000 molecular weight cut-off. The dialyzed solution was centrifuged at 2500×g for 10 minutes, and the resulting pellet was resuspended in 5 ml PBS to form a peptide-LDL immunogen. A peptide-LDL immunogen was prepared using the above-described polypeptide, namely $p(141–155)_2$.

b. Immunization and Collection of Polyclonal Antisera

The peptide-LDL immunogen prepared in Example 8a above was emulsified using the Ribi Adjuvant System (Ribi Immunochem Research, Inc., Hamilton, Mont.) according to the manufacturer's instructions. The peptide-LDL antigens were incorporated into the emulsion at a concentration of 300 μg/ml. After preimmune serum samples were collected, two rabbits were injected with 1 ml of a prepared emulsion. The 1 ml emulsion dose was administered as follows: 0.30 ml intradermally (0.05 ml in each of 6 sites); 0.40 ml intramuscularly (0.2 ml into each hind leg); 0.10 ml subcutaneously (in the neck region); and 0.20 ml intraperitoneally. The rabbits were injected 6 times at three-week intervals following the injection protocol as detailed. At one week after the second through sixth injections, blood samples were collected to check antibody titer against the specific peptide used as the immunogen by the SPRIA assay described below. The collected blood samples were stirred in a 37° C. oven for 1 hour, after which the samples are centrifuged at 3000×g for 20 minutes. The interface was collected and spun in a microfuge at 12,000×g for 5 minutes. The supernatant containing anti-peptide antibodies was collected and stored at −20° C.

The peptide antibody titers were determined by solid phase radioimmunoassay (SPRIA) essentially as described in Curtiss and Edgington, *J. Biol. Chem.*, 257:15213–15221 (1982). Briefly, 50 μl of PBS containing 5 μg/ml synthetic peptides were admixed into the wells of microtiter plates. The plates were maintained overnight (about 16 hours) at 4° C. to permit the peptides to adhere to well walls. After washing the wells four times with SPRIA buffer (2.68 mM KCL, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 μl of SPRIA buffer containing 3% normal goat serum (NGS) and 3% bovine serum albumin (BSA) were admixed to each well to block excess protein binding sites. The plates were maintained for 30 minutes at 20° C., the wells emptied by shaking, and blotted dry to form a solid-support, i.e., a solid matrix to which an apo E polypeptide was operatively affixed.

To each well was then admixed 50 μl of a serum supernatant containing anti-peptide antibodies for testing by SPRIA form a solid-liquid phase immunoreaction admixture. The admixture was maintained for 2 hours at 37° C. to permit formation of solid-phase immunoreaction products. After washing the wells as previously described, 50 μl of a second, reveal antibody, $^{125}$I-labeled goat anti-mouse IgG, at 0.25 μg protein per ml were admixed to each well to form a labeling reaction admixture. That admixture was maintained for 1 hour at 37° C. to permit formation of $^{125}$I-labeled solid-phase immunoreaction products. After washing the wells as previously described, the amount of $^{125}$I-labeled product bound to each well was determined by measuring gamma radiation from the labeled product. Specific anti-peptide antibody titers in collected serum samples from immunized rabbits were thus determined and compared to titres measured using pre-immunized normal rabbit serum samples which are a measure of non-specific background. Serum samples are considered to contain anti-peptide polyclonal antibodies if the radioactive signal was 5 times greater than seen with normal rabbit serum.

Anti-apo E polypeptide antibodies were obtained by the above procedure when peptide-LDL immunogens were used that contains the apo E peptide $p(141-155)_2$.

Additional anti-apo E polypeptide antibodies are prepared using peptide-LDL immunogens based on the apo E peptides $p(141-155)_3$ and self-conjugates of $p(141-155)_2$ and $p(141-155)_3$.

The above-described assay is utilized to determine whether this polyclonal antisera binds apo E/VLDL. Apo E/VLDL is prepared as described in Example 8a above. Instead of synthetic peptides, 50 ul of PBS containing 5 ug/ml apo E/VLDL is admixed into the wells of the microtiter plates. SPRIA assays performed in this manner indicate that the antibodies bind apo E/VLDL.

9. Monoclonal Antibody Preparation a. Generation of Hybridomas

Balb/c ByJ mice (Scripps Clinic and Research Foundation Vivarium, La Jolla, Calif.) are immunized intraperitoneally (i.p.) with 50 ug of lipoprotein (polypeptide-carrier complex is used in the case of apo E in complete Freund's adjuvant (CFA) followed by a second immunization in lipoprotein buffer on day 28, 3 days prior to fusion.

The animals immunized with apo E multimeric polypeptide analog, $(p141-155)_2$, conjugated to LDL as described in Example 8a, are sacrificed and the spleen of each mouse is harvested. A spleen cell suspension is then prepared. Spleen cells are then extracted from the spleen cell suspension by centrifugation for about 10 minutes at 1000 r.p.m., at 23 degrees C. Following removal of supernatant, the cell pellet is resuspended in 5 ml cold $NH_4Cl$ lysing buffer, and is incubated for about 10 minutes.

To the lysed cell suspension are admixed 10 ml Dulbecco's Modified Eagle Medium (DMEM) (GIBCO) and HEPES [4-(2-hydroxyethyl)-1-piperidineethanesulfonic acid] buffer, and that admixture is centrifuged for about 10 minutes at 1000 r.p.m. at 23 degrees C.

The supernatant is decanted, the pellet is resuspended in 15 ml of DMEM and HEPES, and is centrifuged for about 10 minutes at 1000 r.p.m. at 23 degrees C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and HEPES, and centrifuged for 10 minutes at 1000 r.p.m. at 23 degrees C.

Spleen cells and myeloma cells are combined in round bottom 15 ml tubes. The cell mixture is centrifuged for 10 minutes at 1000 r.p.m. at 23 degrees C., and the supernatant is removed by aspiration. Thereafter, 200 ul of 50 percent (weight per volume) aqueous polyethylene glycol 4000 molecular weight (PEG; ATCC Baltimore, Md.) at about 37 degrees C. are admixed using a 1 ml pipette with vigorous stirring to disrupt the pellet, and the cells are gently mixed for between 15 and 30 seconds. The cell mixture is centrifuged 4 minutes at 700 r.p.m.

At about 8 minutes from the time of adding the PEG, 5 ml of DMEM plus HEPES buffer are admixed slowly to the pellet, without disturbing the cells. After 1 minute, the resulting admixture is broken up with a 1 ml pipette, and is incubated for an additional 4 minutes. This mixture is centrifuged for 7 minutes at 1000 r.p.m. The supernatant is decanted, 5 ml of HT (hypoxanthine/thymidine) medium are slowly admixed to the pellet, and the admixture is maintained undisturbed for 5 minutes. The pellet is then broken into large chunks, and the final cell suspension is placed into T75 flasks (2.5 ml per flask) into which 7.5 ml HT medium had been placed previously. The resulting cell suspension is incubated at 37 degrees C. to grow the fused cells. After 245 hours 10 ml of HT medium are admixed to the flasks, followed 6 hours later by admixture of 0.3 ml of 0.04 mM aminopterin. 48 hours after fusion, 10 ml of HAT (hypoxanthine/aminopterin/thymidine) medium are admixed to the flasks.

Three days after fusion, viable cells are plated out in 96-well tissue culture plates at about $2\times10^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth was followed microscopically, and culture supernatants were collected about two weeks later and assayed for the presence of antibody molecules that immunoreact with the immunizing polypeptide by solid phase radioimmunoassay (SPRIA) as described in Example 8.

Briefly, 50 ul of PBS containing 5 ug/ml of the immunizing apo E polypeptide of the immunizing apo E polypeptide, $(p141-155)_2$, are admixed into the wells of microtiter plates. The plates are maintained for 3 hours at room temperature to permit the polypeptide to adhere to well walls. After washing the wells four times with SPRIA buffer (2.68 mM KCl, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 ul of SPRIA buffer containing 3% normal goat serum (NGS) and 3% bovine serum albumin (BSA) are admixed to each well to block excess protein binding sites. The plates are maintained for 30 minutes at 20 degrees C., the wells emptied by shaking, and blotted dry to form a solid-support, i.e., a solid matrix to which apo E polypeptide was operatively affixed.

To each well containing an immunizing polypeptide was then admixed 50 ul of hybridoma tissue culture supernatant produced by the corresponding immunizing polypeptide to form a solid-liquid phase immunoreaction admixture. The admixture is maintained for 2 hours at 37 degrees C. to permit formation of solid-phase immunoreaction products. After washing the wells as previously described, 50 ul of $^{125}I$-labeled goat anti-mouse IgG at 0.25 ug protein per ml are admixed to each well to form a labeling reaction admixture. That admixture is maintained for 1 hour at 37 degrees C. to permit formation of $^{125}I$-labeled solid-phase immunoreaction products. After washing the wells as previously described, the amount of $^{125}I$-labeled product bound to each well was determined by measuring gamma radiation from the labeled product. Hybridoma culture supernatants are considered to contain monoclonal anti-apo E polypeptide antibodies if the immunoreaction product formed produced a radioactive signal five times greater than a signal measured using a control hybridoma culture supernatant.

The anti-B-100 monoclonal antibody MB47 was prepared essentially as described above, except that LDL was used as the immunogen, and the antibody was selected by screening for immunoreaction with isolated apo B-100.

b. Isolation of Immunoglobin

Ascites fluids containing monoclonal antibody molecules useful herein were prepared using 10-week-old Balb/c mice. The mice were first primed with 0.3 ml of mineral oil and injected intraperitoneally with $3-50\times10^5$ MB47 hybridoma cells prepared as described in Example 9a. The average time for development of ascites was 12 days. The resulting ascites fluid was collected and clarified by centrifugation at $15,000\times g$ for 1 hour at 4 degrees C. to form clarified ascites fluids, which can be pooled and stored if desired, at −20 degrees C.

Isolated MB47 monoclonal antibody molecules were prepared by chromatography of the clarified ascites fluids on a protein A-Sepharose 4B column (Pharmacia Fine Chemicals, Piscataway, N.J.). Antibody was eluted from the column with 0.1 molar (M) acetic acid to form the isolated monoclonal antibody MB47.

Isolated monoclonal antibody molecules were also prepared by fast protein liquid chromatography (FPLC) of a clarified ascites fluid on a Pharmacia Mono Q HR 5/5 anion exchange column in a Pharmacia FPLC System using a 0–0.5M NaCl gradient in 10 mM Tris, pH 8.0, and following the directions supplied with the column. The resulting isolated monoclonal antibody molecules were concentrated using an Amicon stirred ultrafiltration cell (Danvers, Mass.; PM 30 membrane) to a concentration of 1 mg/ml, dialyzed into PBS (phosphate-buffered saline, pH 7.2) and stored at −70 degrees C. to form purified monoclonal antibody.

Monoclonal anti-apo E polypeptide antibody molecules can be purified as above using the hybridoma that can be prepared by the methods of Example 9a to form purified anti-apo E polypeptide monoclonal antibody.

10. Solid-Phase Polypeptide ELISA

Apo E polypeptides prepared in Example 1 immunoreact with an anti-apo E polypeptide antibody in a direct binding ELISA. In the assay, 50 μg/ml of a polypeptide-containing solution of $(p141-155)_2$ is dissolved in PBS to form a peptide coating solution, of which 150 μl is admixed into the wells of a microtiter plate. The wells are then maintained for about 16 to 20 h at 4° C. to permit the peptide to adsorb onto (coat) the walls of the wells. After removing the peptide coating solution by shaking, the wells are washed once with 350 μl of rinsing buffer (PBS containing 1 g/l BSA, 0.5 ml/l Tween 20, and 2 μl/l aprotinin). Excess protein binding sites are blocked by admixing 200 μl of blocking buffer (PBS containing 3% BSA) into each well, maintaining the wells for 1 hour at 37° C., removing the blocking buffer by shaking, and then washing the wells 3 times as previously described. The plate is then dried for 1 hour at 37° C. followed by addition of 100 μl of PBS containing 0.5 μg/ml horseradish peroxidase-conjugated anti-$(p141-155)_2$ antibody, prepared according to the method of Nakane, et al., *J. Histochem. Cytochem.*, 22:1084 (1974), to form a solid-liquid phase immunoreaction admixture. The resulting solid-liquid phase immunoreaction admixture is maintained at 20° C. for 1 hour to permit formation of a solid-phase polypeptide-containing immunoreaction product. The wells are then washed 3 times with rinsing buffer to remove unbound antibody.

Assays are performed in identical manner using anti-$p(141-155)_3$ polyclonal antibodies, which are elicited as previously described and conjugated to horseradish peroxidase.

The amount of immunoreaction product present in the solid phase is then determined by admixing two hundred microliters of OPD substrate (3% $H_2O_2$ and 0.67 mg/ml o-phenylene diamine) into each well to form a developing-reaction admixture. The admixture is maintained for 30 minutes at about 20° C. Subsequently, 50 μl of 4N $H_2SO_4$ are admixed into each well to stop the developing-reaction, and the resulting solution is assayed for absorbance at 450 nanometers using a microtiter plate reader (Dynatech) to detect the amount of formed immunoreaction product.

In order to determine specificity of the antibody molecules using the same assay, a monomer peptide, p141–155, is prepared as described in Example 1 and tested as above. Additionally, control peptides p93–112 and p172–182 are prepared and tested. The results in all cases indicate that these antibodies do not bind either the monomer or the control peptides.

A competition ELISA is useful to detect apo E polypeptide or apo E in a fluid sample such as serum. Microtiter plates are coated with the dimer $p(141-155)_2$ as described hereinbefore. After the drying step of the assay described hereinbefore, 50 μl of a fluid sample (i.e., an apo E polypeptide-containing or an apo E-containing fluid sample) or standard (i.e., an apo E polypeptide as a standard) to be assayed are admixed into the polypeptide-coated well simultaneously with 50 μl of HRPO-conjugated anti-peptide antibody to form an immunoreaction admixture. In the assay described herein, two competitors (polypeptide standard or the fluid sample) are tested in separate immunoreaction admixtures for their ability to compete for binding of the anti-apo E antibody to the coated polypeptide analog over a range of antibody dilutions. The polypeptide standard in solution is added at a starting concentration of 1 mg/ml and serially diluted to a final concentration of 0.0156 mg/ml. Serum or plasma fluid samples are added at a starting dilution of 1:10 and diluted serially to a final dilution of 1:320. The plate is then incubated for 30 minutes at room temperature, washed and the assay developed as described hereinbefore to determine the amount of immunoreaction product formed, and thereby the amount of competitor present in the added fluid sample.

The competition ELISA is particularly preferred to measure apo E-containing lipoprotein particles in bodily fluid, such as total apo E, and can also be used to monitor the fate of therapeutically administered apo E polypeptide present in the serum of a patient after administration of therapeutic apo E polypeptide compositions.

(1) APO E SANDWICH ASSAY

Described herein is a capture or sandwich assay. Polystyrene microtiter plates (Nunc-Immuno Plate I) are coated with 150 ul of sodium bicarbonate buffer, pH 9.0, containing 1 ug/ml of purified anti-$p(141-155)_3$ polyclonal antibody for 16 hours at 4° C. to prepare a solid-phase capture antibody. The plates are washed 3 times with PBS containing 0.1% BSA, 0.05% Tween, and then blocked with 3% BSA exactly as described above. The apo E/VLDL standard (prepared as in Example 8) is diluted 1:200 in PBS containing 0.5% (Diluting buffer=LPDP/PBS) to concentrations ranging from 0.125 to 4.0 ug/ml. The same controls as described above for the competition ELISA are used in this assay. Plasma or serum samples and controls are diluted 1000-fold in dilution buffer. Fifty ul of standards and unknown samples are added to the wells in triplicate.

The plates are incubated exactly 30 minutes at 25° C., and the liquid phase is removed from the wells. Fifty ul of PBS, containing a fixed concentration of HRPO-linked anti-B100 monoclonal reveal antibody (MB47), described before, is immediately pipetted into wells containing aliquot 1 of the plasma samples. The plates are incubated exactly 30 minutes at 25° C., washed, and 100 ul of OPD substrate solution are added for an additional 30 minute incubation at 25° C. Color development is stopped by addition of 50 ul of 4N $H_2SO_4$ and plates are read in a microplate reader as described before.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

What is claimed is:

1. A composition comprising antibody molecule that specifically bind:

(a) a polypeptide comprising two to ten segments, each segment having an amino acid residue sequence represented by the formula:

Leu—Arg—Lys—Leu—Arg—Lys—
Arg—Leu—Leu—Arg—Asp—Ala—Asp—Asp—
Leu, and (b) apolipoprotein E/very low density lipoprotein (apo E/VLDL), but do not specifically bind a polypeptide comprising the amino acid residue sequence:

LSKELQAAQARLGADMEDVR or RGLSAIRERL.

and do not specifically bind a polypeptide comprising a single segment having an amino acid residue sequence represented by the formula:

Leu—Arg—Lys—Leu—Arg—Lys—
Arg—Leu—Leu—Arg—Asp—Ala—Asp—Asp—
Leu.

2. The composition of claim 1 wherein said polypeptide in (a) is a tandem dimer.

3. The composition of claim 1 wherein said polypeptide in (a) is a self-conjugate.

4. A method for determining the amount of an apo E antigen in a vascular fluid sample, comprising the steps of (a) admixing a vascular fluid sample with an anti-apo E antibody to form an immunoreaction admixture, said antibody comprising antibody molecules that specifically bind:

(i) a polypeptide comprising two to ten segments each having an amino acid residue sequence represented by the formula:

Leu—Arg—Lys—Leu—Arg—Lys—
Arg—Leu—Leu—Arg—Asp—Ala—Asp—Asp—
Leu, and (ii) apo E/VLDL, but do not specifically bind a polypeptide comprising the amino acid residue sequence LSKELQAAQARLGADMEDVR or RGLSAIRERL, and do not specifically bind a polypeptide comprising a single segment having an amino acid residue sequence represented by the formula:

Leu—Arg—Lys—Leu—Arg—Lys—
Arg—Leu—Leu—Arg—Asp—Ala—Asp—Asp—

-continued

Leu:

(b) maintaining said immunoreaction admixture under biological assay conditions for a time period sufficient to form an apo E-containing immunoreaction product; and (c) detecting the amount of said immunoreaction product formed in step (b) and thereby the amount of apo E antigen present in said vascular fluid sample.

5. The method of claim 4 wherein said antibody is operatively linked to a solid support such that said immunoreaction admixture has both a liquid phase and a solid phase, and the immunoreaction product formed in step (b) is present in the solid phase.

6. The method of claim 4 wherein said immunoreaction product is detected according to step (c) by:

(i) admixing a labeled specific binding agent which binds an apo E-containing particle with said apo E-containing immunoreaction product to form a labeling reaction admixture, wherein said specific binding agent comprises a monoclonal anti-B-100 antibody;

(ii) maintaining said labeling reaction admixture under biological assay conditions for a time period sufficient for said labeled specific binding agent to bind the apo E-containing immunoreaction product and form a labeled complex; and (iii) detecting the amount of any labeled complex formed, and thereby the amount of said apo E-containing immunoreaction product.

7. The method of claim 6 wherein said monoclonal anti-B-100 antibody is produced by the hybridoma having ATCC designation HB 8742.

8. A method for determining the amount of an apo E antigen in a vascular fluid sample, comprising the steps of:

(a) admixing a vascular fluid sample with a solid phase-bound apo E polypeptide comprising two to ten segments each having an amino acid residue sequence represented by the formula:

Leu—Arg—Lys—Leu—Arg—Lys—
Arg—Leu—Leu—Arg—Asp—Ala—Asp—Asp—
Leu.

to form a first solid-liquid phase admixture;

(b) admixing said first solid-liquid phase admixture with an antibody, said antibody comprising a limiting amount of anti-apo E polypeptide antibody molecules that specifically bind:

(i) a polypeptide comprising two to ten segments each having an amino acid residue sequence represented by the formula:

Leu—Arg—Lys—Leu—Arg—Lys—
Arg—Leu—Leu—Arg—Asp—Ala—Asp—Asp—
Leu. and (ii) apo E/VLDL, but do not specifically bind a polypeptide comprising the amino acid residue sequence LSKELQAAQARLGADMEDVR or RGLSAIRERL, and do not specifically bind a polypeptide comprising a single segment having an amino acid residue sequence represented by the formula:

Leu—Arg—Lys—Leu—Arg—Lys—
Arg—Leu—Leu—Arg—Asp—Ala—Asp—Asp—
Leu.

to form a second admixture;

(c) maintaining said second admixture under biological assay conditions for a period of time sufficient to form an apo E-containing immunoreaction product in the solid phase; and (d) determining the amount of immunoreaction product present in the solid phase formed in step (c), and thereby the amount of said apo E in said fluid.

9. The method of claim 8 wherein said anti-apo E polypeptide antibody in step (b) is operatively linked to an enzyme indicating means, and said product formed in step (c) is a labeled immunoreaction product.

10. A diagnostic system, in kit form, comprising, in an amount sufficient to perform at least one assay, an antibody comprising anti-apo E antibody molecules that specifically bind:

(a) a polypeptide comprising two to ten segments each having an amino acid residue sequence comprising the formula:

Leu—Arg—Lys—Leu—Arg—Lys—
Arg—Leu—Leu—Arg—Asp—Ala—Asp—Asp—
Leu. and (b) apo E/VLDL, but do not specifically bind a polypeptide comprising the amino acid residue sequence LSKELOAAOARLGADMEDVR or RGLSAIRERL, and do not specifically bind a polypeptide comprising a single segment having an amino acid residue sequence represented by the formula:

Leu—Arg—Lys—Leu—Arg—Lys—
Arg—Leu—Leu—Arg—Asp—Ala—Asp—Asp—
Leu, wherein said anti-apo E antibody is operatively linked to a solid matrix.

11. The diagnostic system of claim 10 which further comprises a reveal antibody comprising antibody molecules that immunoreact with apo E/VLDL particles, wherein said antibody molecules immunoreact with apo B-100.

12. The diagnostic system of claim 11 wherein said reveal antibody is operatively linked to an enzyme indicating means.

13. The diagnostic system of claim 11 wherein said antibody molecules that immunoreact with apo B-100 are produced by the hybridoma having ATCC designation HB 8746.

14. A diagnostic system, in kit form, comprising, in an amount sufficient to perform at least one assay, a polypeptide comprising two to ten segments each having an amino acid residue sequence represented by the formula:

Leu—Arg—Lys—Leu—Arg—Lys—
Arg—Leu—Leu—Arg—Asp—Ala—Asp—Asp—
Leu, and further comprising antibody molecules that specifically bind:

(a) a polypeptide comprising two to ten segments, each segment having an amino acid residue sequence represented by the formula:

Leu—Arg—Lys—Leu—Arg—Lys—
Arg—Leu—Leu—Arg—Asp—Ala—Asp—Asp—
Leu. and (b) apolipoprotein E/very low density lipoprotein (apo E/VLDL), but do not specifically bind a polypeptide comprising the amino acid residue sequence: LSKELOAAOARLGADMEDVR or RGLSAIRERL, and do not specifically bind a polypeptide comprising a single segment having an amino acid residue sequence represented by the formula:

Leu—Arg—Lys—Leu—Arg—Lys—
Arg—Leu—Leu—Arg—Asp—Ala—Asp—Asp—
Leu.

15. The diagnostic system of claim 14 wherein said antibody molecules are operatively linked to a solid support.

* * * * *